United States Patent
Peltier et al.

(10) Patent No.: US 10,973,710 B2
(45) Date of Patent: Apr. 13, 2021

(54) ABSORBENT ARTICLE AND FASTENING LAMINATE

(71) Applicant: 3M INNOVATIVE PROPERTIES COMPANY, St. Paul, MN (US)

(72) Inventors: Mark A. Peltier, Forest Lake, MN (US); Timothy V. Stagg, Hudson, WI (US); Leigh E. Wood, Woodbury, MN (US); Thomas J. Gilbert, St. Paul, MN (US); Steven J. Perron, St. Paul, MN (US)

(73) Assignee: 3M Innovative Properties Company, St. Paul, MN (US)

(*) Notice: Subject to any disclaimer, the term of this patent is extended or adjusted under 35 U.S.C. 154(b) by 846 days.

(21) Appl. No.: 15/527,570

(22) PCT Filed: Nov. 17, 2015

(86) PCT No.: PCT/US2015/061046
§ 371 (c)(1),
(2) Date: May 17, 2017

(87) PCT Pub. No.: WO2016/081438
PCT Pub. Date: May 26, 2016

(65) Prior Publication Data
US 2017/0354553 A1    Dec. 14, 2017

Related U.S. Application Data

(60) Provisional application No. 62/080,681, filed on Nov. 17, 2014.

(51) Int. Cl.
*A61F 13/15* (2006.01)
*A61F 13/20* (2006.01)
(Continued)

(52) U.S. Cl.
CPC ........ *A61F 13/622* (2013.01); *A61F 13/5622* (2013.01); *A61F 13/62* (2013.01); *A61F 13/15756* (2013.01); *A61F 13/627* (2013.01)

(58) Field of Classification Search
USPC ........................................................ 604/391
See application file for complete search history.

(56) References Cited

U.S. PATENT DOCUMENTS 3,848,594 A     11/1974   Buell
4,127,132 A *   11/1978   Karami ................... A61F 13/58
                                                        604/390
(Continued)

FOREIGN PATENT DOCUMENTS

DE          29522180          4/2000
EP           341993           8/1993
(Continued)

OTHER PUBLICATIONS

International Search Report for PCT International Application No. PCT/US2015/061046, dated Feb. 23, 2016, 4 pages.

*Primary Examiner* — Michele M Kidwell
(74) *Attorney, Agent, or Firm* — Kathleen B. Gross

(57) ABSTRACT

Absorbent article including a chassis and fastening tab. The fastening tab includes a carrier, a first fastener having first male fastening elements, and a second fastener. The second fastener includes a backing with first and second opposing surfaces, with second male fastening elements on the first surface. A first portion of the second surface of the backing is connected to the carrier, and a second portion of the second surface of the backing is attached to the topsheet side of the chassis. The carrier is attached to the backsheet side of the chassis. Some fastening laminates, before attachment to the article, have the second portion of the second fastener folded over to face the first portion of the second fastener.

(Continued)

Other laminates have the second fastener positioned with its first surface toward the carrier and attached to the carrier with a film.

20 Claims, 5 Drawing Sheets

(51) Int. Cl.
  *A61F 13/62* (2006.01)
  *A61F 13/56* (2006.01)

(56) References Cited

U.S. PATENT DOCUMENTS

| | | | |
|---|---|---|---|
| 4,178,933 A * | 12/1979 | Nemeth | A61F 13/58 |
| | | | 604/390 |
| 4,699,622 A | 10/1987 | Toussant | |
| 4,775,310 A | 10/1988 | Fischer | |
| 4,869,724 A * | 9/1989 | Scripps | A61F 13/5512 |
| | | | 604/389 |
| 4,894,060 A | 1/1990 | Nestegard | |
| 5,077,870 A | 1/1992 | Melbye | |
| 5,288,546 A * | 2/1994 | Roessler | A61F 13/58 |
| | | | 428/40.1 |
| 5,300,058 A | 4/1994 | Goulait | |
| 5,537,722 A | 7/1996 | Niederhofer | |
| 5,549,591 A * | 8/1996 | Landvogt | A61F 13/581 |
| | | | 604/389 |
| 5,554,146 A | 9/1996 | Niederhofer | |
| 5,571,097 A | 11/1996 | Seth | |
| 5,605,729 A | 2/1997 | Mody | |
| 5,605,735 A * | 2/1997 | Zehner | A61F 13/622 |
| | | | 428/100 |
| 5,692,271 A | 12/1997 | Provost | |
| 5,722,127 A | 3/1998 | Coates | |
| 5,851,205 A | 12/1998 | Hisada | |
| 5,897,546 A | 4/1999 | Kido | |
| 5,926,926 A * | 7/1999 | Kato | A61F 13/622 |
| | | | 24/442 |
| 5,957,908 A | 9/1999 | Kline | |
| 6,030,373 A | 2/2000 | VanGompel | |
| 6,075,179 A | 6/2000 | McCormack | |
| 6,146,369 A | 11/2000 | Hartman | |
| 6,190,594 B1 | 2/2001 | Gorman | |
| 6,190,758 B1 | 2/2001 | Stopper | |
| 6,287,665 B1 | 9/2001 | Hammer | |
| 6,363,587 B1 * | 4/2002 | Richter | A61F 13/622 |
| | | | 24/306 |
| 6,419,667 B1 | 7/2002 | Avalon | |
| 6,489,003 B1 | 12/2002 | Levitt | |
| 6,575,953 B2 | 6/2003 | Olson | |
| 6,627,133 B1 | 9/2003 | Tuma | |
| 6,994,698 B2 | 2/2006 | Leak | |
| 7,032,278 B2 | 4/2006 | Kurtz, Jr. | |
| 7,048,818 B2 | 5/2006 | Krantz | |
| 7,125,400 B2 | 10/2006 | Igaue | |
| 7,198,743 B2 | 4/2007 | Tuma | |
| 7,214,334 B2 | 5/2007 | Jens | |
| 7,219,403 B2 | 5/2007 | Miyamoto | |
| 7,223,314 B2 | 5/2007 | Provost | |
| 7,371,302 B2 | 5/2008 | Miyamoto | |
| 7,407,496 B2 | 8/2008 | Petersen | |
| 7,444,722 B2 | 11/2008 | McDaniel | |
| 7,578,813 B2 * | 8/2009 | Mitsui | A61F 13/625 |
| | | | 604/385.28 |
| 8,496,640 B2 * | 7/2013 | Molander | A61F 13/622 |
| | | | 604/389 |
| 9,155,669 B2 | 10/2015 | Petersen | |
| 10,085,897 B2 * | 10/2018 | Landgrebe | A61F 13/56 |
| 10,548,783 B2 | 2/2020 | Peiffer | |
| 10,709,619 B2 * | 7/2020 | Chandrasekaran | A61F 13/56 |
| 2002/0016581 A1 | 2/2002 | Kline | |
| 2004/0261230 A1 | 12/2004 | Neeb | |
| 2004/0261233 A1 | 12/2004 | Kingsford | |
| 2006/0069377 A1 * | 3/2006 | Calvert | A61F 13/5633 |
| | | | 604/391 |
| 2006/0293635 A1 * | 12/2006 | Petersen | A61F 13/625 |
| | | | 604/385.03 |
| 2007/0134489 A1 | 6/2007 | Neugebauer | |
| 2007/0173781 A1 * | 7/2007 | Jackson | A61F 13/15756 |
| | | | 604/391 |
| 2007/0286976 A1 * | 12/2007 | Selen | A61F 13/15756 |
| | | | 428/42.2 |
| 2008/0097368 A1 * | 4/2008 | Molander | A61F 13/581 |
| | | | 604/391 |
| 2011/0004182 A1 * | 1/2011 | Hilston | A61F 13/15756 |
| | | | 604/391 |
| 2011/0147475 A1 | 6/2011 | Biegler | |
| 2011/0151171 A1 | 6/2011 | Biegler | |
| 2011/0313389 A1 | 12/2011 | Wood | |
| 2012/0204383 A1 | 8/2012 | Wood | |
| 2014/0332999 A1 | 11/2014 | Rothwell | |
| 2016/0128877 A1 * | 5/2016 | Chandrasekaran | A61F 13/622 |
| | | | 24/306 |
| 2016/0143792 A1 | 5/2016 | Peiffer | |

FOREIGN PATENT DOCUMENTS

| | | |
|---|---|---|
| EP | 539504 | 2/1997 |
| JP | 2597850 | 9/1997 |
| JP | 3479395 | 12/2003 |
| JP | 2010-29532 | 2/2010 |
| JP | 2010-131256 | 6/2010 |
| JP | 2010-148762 | 7/2010 |
| JP | 2011-072430 | 4/2011 |
| WO | WO 1999-053881 | 10/1999 |
| WO | WO 2000-027236 | 5/2000 |
| WO | WO 00/50229 | 8/2000 |
| WO | WO 2011-163020 | 12/2011 |
| WO | WO 2013-172957 | 11/2013 |
| WO | WO 2013-172960 | 11/2013 |
| WO | WO 2014-002433 | 1/2014 |

* cited by examiner

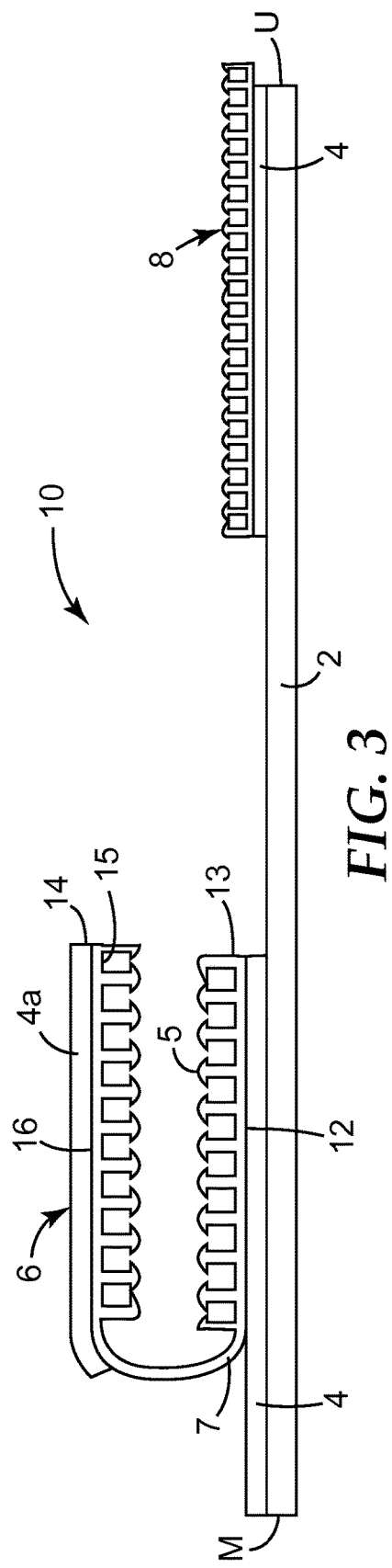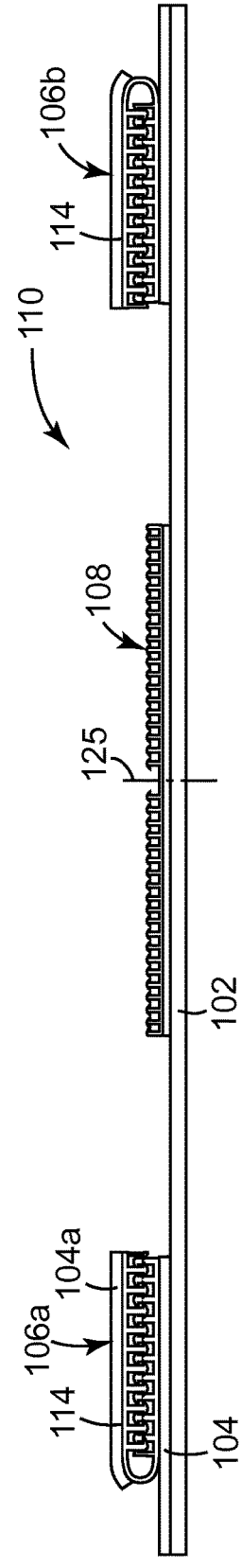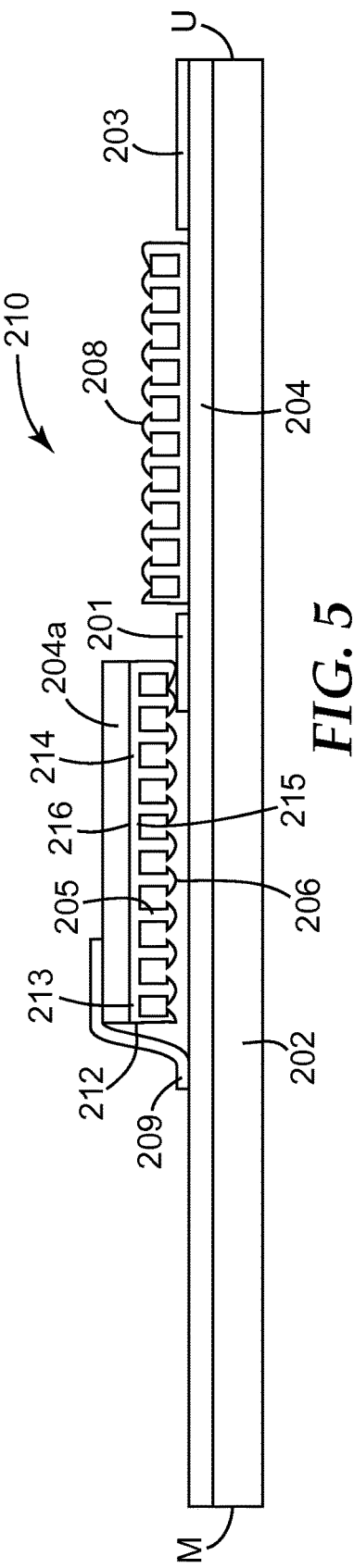

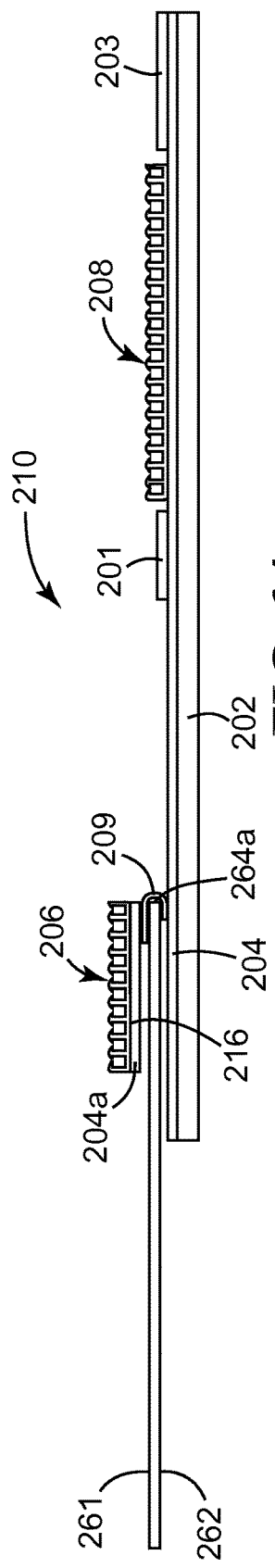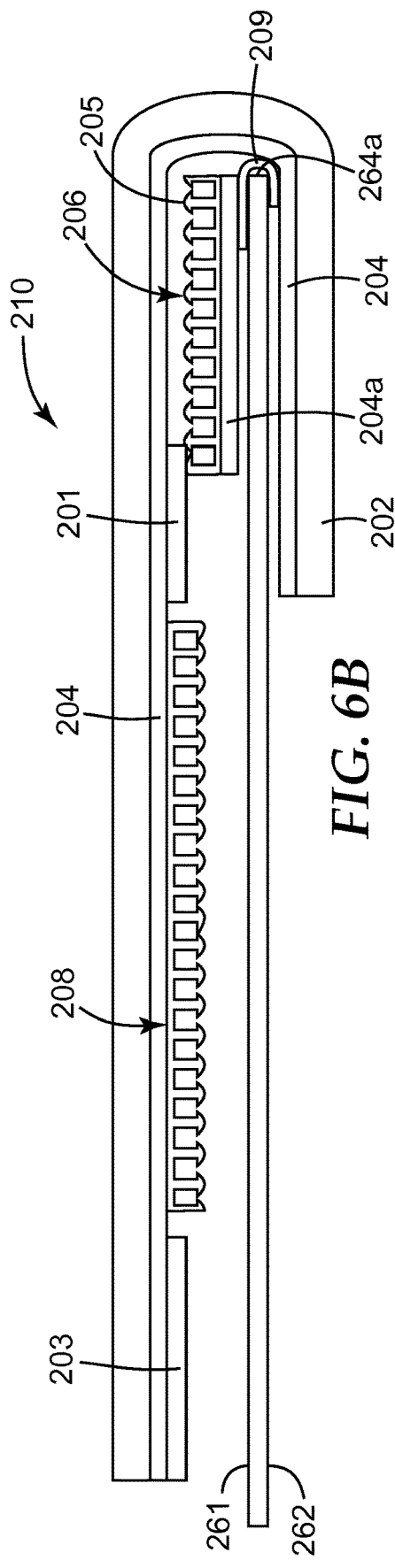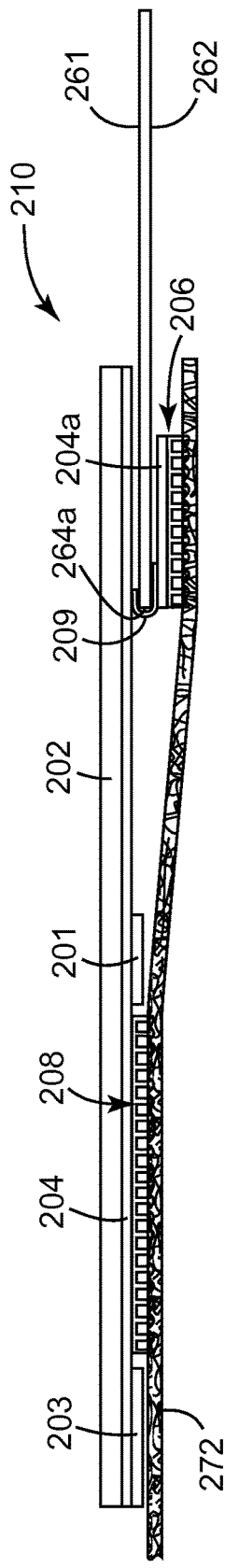

ABSORBENT ARTICLE AND FASTENING LAMINATE

CROSS REFERENCE TO RELATED APPLICATION

This application is a national stage filing under 35 U.S.C. 371 of PCT/US2015/061046, filed Nov. 17, 2015, which claims priority to U.S. Provisional Application No. 62/080,681, filed Nov. 17, 2014, the disclosure of which is incorporated by reference herein in its entirety.

BACKGROUND

Mechanical fasteners, which are also called hook and loop fasteners, are useful for providing releasable attachment in numerous applications. For example, mechanical fasteners are widely used in wearable absorbent articles to fasten such articles around the body of a person. In typical configurations, a hook strip or patch on a fastening tab attached to the rear waist portion of a diaper or incontinence garment, for example, can fasten to a landing zone of loop material on the front waist region, or the hook strip or patch can fasten to the backsheet (e.g., nonwoven backsheet) of the diaper or incontinence garment in the front waist region. Absorbent articles often employ woven or nonwoven materials, for example, to provide a cloth-like feeling in order to increase the comfort of wearing.

Fastening tabs often have a manufacturer's end that is attached to the rear waist region of an absorbent article and a user's end that can be grasped and extends outwardly beyond the edge of an absorbent article before it is attached to the front waist region of the absorbent article. The attachment point of the tab at the manufacturer's end must be strong enough to withstand the force applied during the application and wearing of the absorbent article; otherwise the tab can separate from the absorbent article during use. So called Y-bonded fastening tabs are proposed to have strong attachment to absorbent articles; see, e.g., U.S. Pat. No. 3,848,594 (Buell).

Some fastening tabs have more than one region of mechanical fastener (e.g., hook patches) on the tab, which has been proposed to decrease the likelihood of unintentional disengagement of the mechanical fastener members. See, for example, U.S. Pat. No. 5,957,908 (Kline et al.) and U.S. Pat. No. 5,851,205 (Hisada et al.).

SUMMARY

The present disclosure provides an absorbent article including a chassis and a fastening tab bonded to an edge of the chassis. The fastening tab has at least two mechanical fasteners, one of which is on the user's end of the fastening tab while the other, together with a carrier for the fastening tab, forms a Y-bond on the edge of the absorbent article.

In one aspect, the present disclosure provides an absorbent article including a chassis and a fastening tab. The chassis has a topsheet side, a backsheet side, and first and second opposing longitudinal edges extending from a rear waist region to an opposing front waist region. The fastening tab includes a carrier, a first mechanical fastener having first male fastening elements, and a second mechanical fastener. The first mechanical fastener is disposed on the carrier. The second mechanical fastener includes a backing having a first surface and a second surface opposite the first surface. For a first portion of the backing, the second surface of the backing is connected to the carrier, and for a second portion of the backing, the second surface of the backing is attached to the first longitudinal edge of the chassis on the topsheet side. The carrier is attached to the first longitudinal edge of the chassis on the backsheet side. For at least one of the first portion or second portion of the backing, second male fastening elements are disposed on the first surface of the backing.

In another aspect, the present disclosure provides a fastening laminate including a carrier, a first mechanical fastener having first male fastening elements, and a second mechanical fastener. The first mechanical fastener is disposed on the carrier. The second mechanical fastener includes a backing having a first surface and a second surface opposite the first surface, with second male fastening elements on the first surface of the backing on at least a first portion of the backing or a second portion of the backing. For a first portion of the backing, the second surface of the backing is attached to the carrier at a location that does not include an edge of the carrier while for the second portion of the backing, the backing is not attached to the carrier but is folded over so that at least part of the first surface of the second portion of the backing faces at least part of the first surface of the first portion of the backing.

In another aspect, the present disclosure provides a fastening laminate including a carrier, a first mechanical fastener having first male fastening elements, and a second mechanical fastener. The first mechanical fastener is disposed on the carrier. The second mechanical fastener includes a backing having a first surface and a second surface opposite the first surface, with second male fastening elements on the first surface of the backing. The second mechanical fastener is positioned with its first surface toward the carrier. An attachment film is adhesively attached to a first portion of the second surface of the backing and to the carrier, but the second surface of the backing is not otherwise attached to the carrier.

In any of the fastening laminates of the aforementioned aspects, the carrier has opposing first and second edges. The first portion of the second surface of the backing of the second mechanical fastener is attached to the carrier at a location that does not include the first edge of the carrier and is positioned between the first edge of the carrier and the first mechanical fastener.

The fastening tabs according to the present disclosure and/or on absorbent articles according to the present disclosure can be attached securely to the chassis and may provide robust engagement with complementary mechanical fastening patches due to, for example, the first and second mechanical fasteners. Also, since the second mechanical fastener is inboard of the edge of the chassis, while the first mechanical fastener is on the user's end portion of the fastening tab, the fastening tabs disclosed herein may resist shifting forces such as torsional or rotational forces caused by movement of the wearer of the absorbent article. Since Y-bonded fastening tabs generally require a second film to attach a primary tab to the edge of an article, the present disclosure provides a fastening tab with additional fastening function without introducing additional components or manufacturing steps.

In this application:

Terms such as "a", "an" and "the" are not intended to refer to only a singular entity, but include the general class of which a specific example may be used for illustration. The terms "a", "an", and "the" are used interchangeably with the term "at least one".

The phrase "comprises at least one of" followed by a list refers to comprising any one of the items in the list and any combination of two or more items in the list. The phrase "at least one of" followed by a list refers to any one of the items in the list or any combination of two or more items in the list.

The term "machine direction" (MD) as used herein denotes the direction of a running, continuous web during the manufacturing of the absorbent article disclosed herein. In a roll, for example, comprising a carrier web and a fastening strip, the machine direction corresponds to the longitudinal direction of the roll. Accordingly, the terms machine direction and longitudinal direction may be used herein interchangeably. The term "cross-direction" (CD) as used herein denotes the direction that is essentially perpendicular to the machine direction. When a portion of the laminate disclosed herein is cut from a roll, the cross-direction corresponds to the width of the roll.

The terms "first", "second", and "third" are used in this disclosure. It will be understood that, unless otherwise noted, those terms are used in their relative sense only. For these components, the designation of "first", "second", and "third" may be applied to the components merely as a matter of convenience in the description of one or more of the embodiments.

All numerical ranges are inclusive of their endpoints and nonintegral values between the endpoints unless otherwise stated (e.g. 1 to 5 includes 1, 1.5, 2, 2.75, 3, 3.80, 4, and 5).

The above summary of the present disclosure is not intended to describe each disclosed embodiment or every implementation of the present disclosure. The description that follows more particularly exemplifies illustrative embodiments. It is to be understood, therefore, that the drawings and following description are for illustration purposes only and should not be read in a manner that would unduly limit the scope of this disclosure.

BRIEF DESCRIPTION OF THE DRAWINGS

The disclosure may be more completely understood in consideration of the following detailed description of various embodiments of the disclosure in connection with the accompanying drawings, in which:

FIG. 3 is a cross-section of the embodiment shown in FIGS. 2A to 2C before application to the absorbent article;

FIG. 4 is a cross-section of an embodiment of a fastening laminate useful for making an absorbent article according to the method of the present disclosure;

FIG. 5 is a cross-section of another embodiment of a fastening laminate according to the present disclosure that is not attached to an absorbent article;

FIG. 6A is a cross-section of a portion of an absorbent article according to the present disclosure in which the fastening laminate shown in FIG. 5 is attached to an absorbent article and is in an open position;

FIG. 6B is a cross-section of a portion of an absorbent article according to the present disclosure in which the fastening laminate shown in FIG. 5 is attached to an absorbent article but configured for storage before use;

FIG. 6C is a cross-section of a portion of an absorbent article according to the present disclosure in which the fastening laminate shown in FIG. 6A is fastened to the front waist region of the absorbent article;

DETAILED DESCRIPTION

Figure 1:
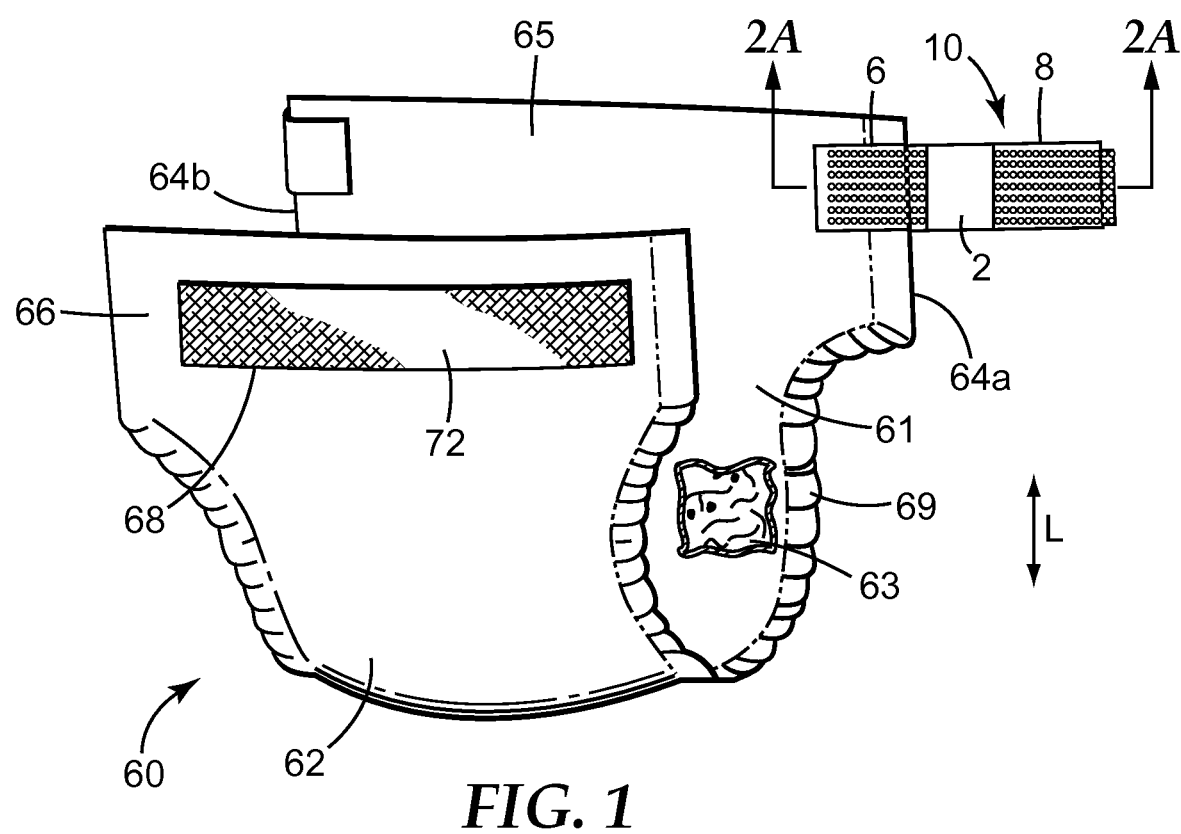
FIG. 1 is a schematic, perspective view of one embodiment of an absorbent article according to the present disclosure.

Reference will now be made in detail to embodiments of the disclosure, one or more examples of which are illustrated in the drawings. Features illustrated or described as part of one embodiment can be used with other embodiments to yield still a third embodiment. It is intended that the present disclosure include these and other modifications and variations.

Absorbent articles according to the present disclosure include diapers and adult incontinence articles, for example. A schematic, perspective view of one embodiment of an absorbent article 60 according to the present disclosure is shown in FIG. 1. Absorbent article 60 includes a chassis with a topsheet side 61 and a backsheet side 62. The chassis also has first and second opposing longitudinal edges 64a and 64b extending from a rear waist region 65 to an opposing front waist region 66. The longitudinal direction of the absorbent article 60 refers to the direction "L" extending between the rear waist region 65 and the front waist region 66. Therefore, the term "longitudinal" refers to the length of the absorbent article 60, for example, when it is in an open configuration.

At least one of the front waist region 66 or the rear waist region 65, more typically the rear waist region 65, comprises at least one fastening tab 10. The fastening tab 10 includes a carrier 2 and first and second discrete mechanical fasteners 6 and 8. The first mechanical fastener 8 is located on a portion of the first surface of the carrier 2, generally toward the edge of the user's end of the fastening tab.

Figure 2A:
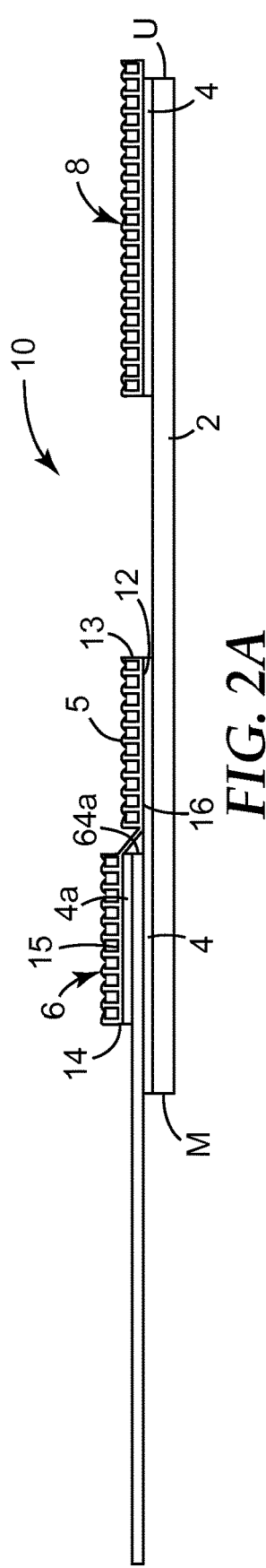
FIG. 2A is an example of a cross-section taken through line 2A-2A in FIG. 1.

The second mechanical fastener 6 is also shown in the cross-section shown in FIG. 2A. The second mechanical fastener 6 includes a backing 12 having a first portion 13 and a second portion 14. The backing 12 and consequently each of the first portion 13 and second portion 14 have a first surface 15, and a second surface 16 opposite the first surface 15, with upstanding male fastening elements 5 on the first surface 15 of the backing 12. Male fastening elements 5 on the second mechanical fastener 6 are herein referred to as the second male fastening elements. The second surface 16 of the second portion 14 of the backing 12 is attached to the first longitudinal edge 64a of the chassis in the rear waist region 65 on the topsheet side 61. The carrier is attached to the first longitudinal edge 64a of the chassis in the rear waist region 65 on the backsheet side 62. In the illustrated embodiment, the second surface 16 of the first portion 13 of the backing 12 is attached to the carrier 2. Thus, the fastening tab 10 is bonded to the first longitudinal edge 64a of the chassis in the rear waist region 65 using a Y-bond.

In the illustrated embodiment, the first mechanical fastener 8 also includes upstanding male fastening elements on a first surface of a backing, where the backing is not the same backing as that of the second mechanical fastener. The second surface of the first mechanical fastener 8 is attached to the carrier 2. In general, the first mechanical fastener is positioned toward the end (the user's end "U" as illustrated) of the carrier 2. In the illustrated embodiment, the first mechanical fastener 8 extends beyond edge of the carrier 2.

However, in some embodiments, the first mechanical fastener 8 does not extend beyond the edge of the carrier, and in some embodiments, the first mechanical fastener 8 does not extend to the edge of the carrier. An example is shown in FIGS. 5 and 6A to 6C, which are described below.

Figure 2B:
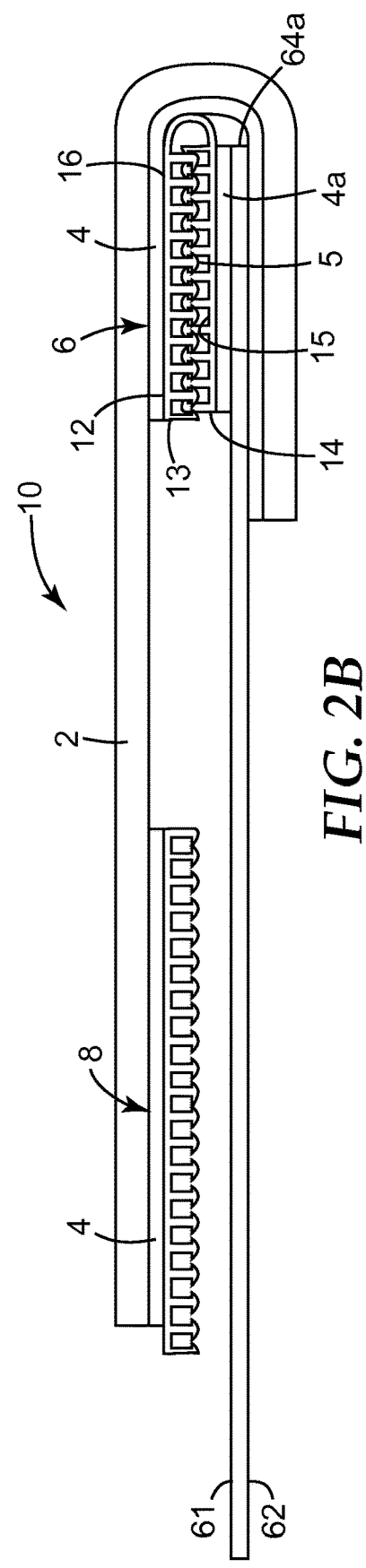
FIG. 2B is a cross-section of the embodiment shown in FIG. 2A but configured for storage before use.

FIG. 2B is a cross-section of fastening tab 10 attached to the absorbent article shown in FIG. 2A but configured for storage before use. As illustrated, the fastening tab 10 is folded at the first longitudinal edge 64a such that the first male fastening elements of the first mechanical fastener 8 contact the topsheet side of the chassis. In this configuration, the backing 12 of the second mechanical fastener 6 is folded over such that at least a portion of the second male fastening elements 5 on the first surface 15 of the first portion 13 abut or are in a face-to-face relation with at least some of the male fastening elements 5 on the first surface 15 of the second portion 14. Although it is not required, in this embodiment, the male fastening elements 5 on the first portion 13 and second portion 14 of the backing 12 can advantageously engage with each other as shown in FIG. 2B to prevent the laminate from popping open during the manufacturing of the absorbent article, for example. It is evident in the illustrated embodiment that the first and second mechanical fasteners 6, 8 do not overlap, but the first male fastening elements of the first mechanical fastener 8 are available to engage with any fibers present on the topsheet side of the absorbent article.

Figure 2C:
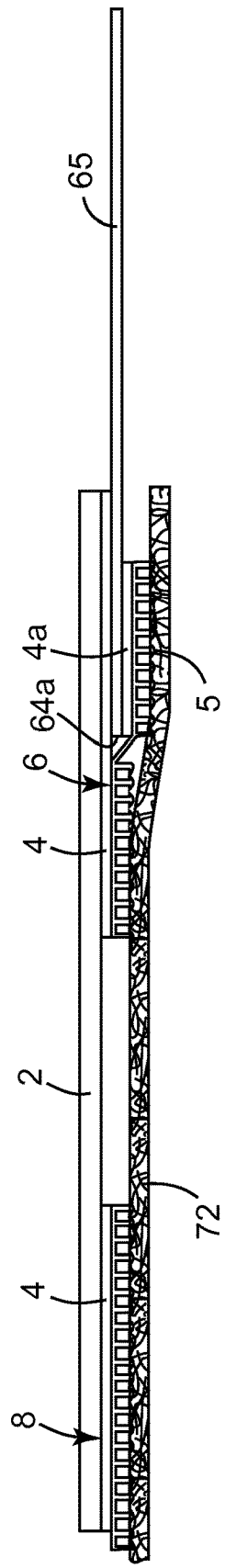
FIG. 2C is a cross-section of the embodiment shown in FIG. 2A but attached to the front waist region of the absorbent article shown in FIG. 1.

FIG. 2C is a cross-section of the embodiment shown in FIG. 2A when the front waist region 66 and the rear waist region 65 of the absorbent article 60 shown in FIG. 1 overlap to encircle the wearer's waist. This is the configuration of the fastening laminate on the absorbent article while the absorbent article is being worn. In the illustrated embodiment a fibrous material 72 positioned on the backsheet 62 of the front waist region 66 provides a target area 68 for the mechanical fasteners 6, 8. Advantageously, both the first mechanical fastener 8 and the second mechanical fastener 6 engage with the fibrous material 72, providing secure attachment. In other embodiments, the size of the target area 68 may be smaller, and the second mechanical fastener 6 may engage with the backsheet while the first mechanical fastener 8 engages with the fibrous material 72. Also, since the second mechanical fastener 6 is located at the longitudinal edge 64a of the absorbent article, while the first mechanical fastener 8 is outboard from the longitudinal edge 64a of the absorbent article, the fastening laminate according to the present disclosure may resist shifting forces such as torsional or rotational forces caused by movement of the wearer of the absorbent article.

A cross-section of the fastening laminate shown in FIGS. 2A to 2C before it is applied to the absorbent article is shown in FIG. 3. FIG. 3 shows an example of the fastening laminate as it may look when it is manufactured. Manufacturing end "M" is the end that becomes permanently attached to the absorbent article, and user's end "U" can be releasably attached to the absorbent article during storage or use. As described above in connection with FIG. 2A, the first mechanical fastener 8 is attached toward one end, typically the user's end "U", of the carrier 2 using adhesive 4. The second mechanical fastener 6 is separated from the first mechanical fastener 8 on the carrier 2. The second surface 16 of the first portion 13 the backing 12 of the second mechanical fastener 6 is attached to the carrier 2. The backing 12 of the second mechanical fastener 6 is folded over such that at least a portion of the second male fastening elements 5 on the first surface 15 of the second portion 14 abut or are in a face-to-face relation with at least some of the male fastening elements 5 on the first surface 15 of the first portion 13. Although it is not shown in FIG. 3, the male fastening elements 5 on the first portion 13 and second portion 14 of the backing 12 can engage with each other as shown in FIG. 2B. In the embodiment illustrated in FIG. 3, there is also a zone 7 between the first portion 13 and the second portion 14 of the second mechanical fastener 6 that is free of fastening elements. This zone 7, although not required, may be useful for allowing the second mechanical fastener 6 to be folded over easily. Referring again to FIG. 1, the fastening laminate in the form of fastening tab 10 may be attached to a longitudinal edge 64a, 64b of an absorbent article 60 by placing the longitudinal edge 64a, 64b on the adhesive 4 at the manufacturing end "M" of the carrier 2 adjacent the second mechanical fastener 6. The second surface 16 of the second portion 14 of the backing 12 is also provided with adhesive 4a. The fastening tab 10 can then be folded over the longitudinal edge 64a, 64b so that adhesive 4a on the second portion 14 of the backing 12 can attach the tab to the topsheet side 61 of the absorbent article as shown in FIG. 2B.

In some embodiments, the fastening laminate according to the present disclosure can be provided as a continuous web, and FIG. 3 may illustrate a cross-section of this continuous web. For example, the laminate can be provided from a roll of a carrier web having first and second mechanical fasteners on the first face of the carrier web. The roll can be unwound into a slitting operation to provide a plurality of the fastening tabs. In the roll, the male fastening elements 5 on the first portion 13 and second portion 14 of the backing 12 would typically engage with each other as shown in FIG. 2B. In these embodiments it can be useful for the second surface of the carrier 2, opposite adhesive portions 4 and 4a, to be provided with a release coating. In some embodiments, the roll includes perforations through the thickness of the mechanical fasteners and the carrier web or other lines of weakness (e.g., partial-depth cut or thinned portion of the carrier web and/or fastening strip) that allows a plurality of individual tab to be separated from the roll. Such lines of weakness may be in the cross-direction of the roll. In other embodiments, slitting the roll after unwinding provides a plurality of the fastening tabs.

In some embodiments, fastening laminate according to the present disclosure can be provided in a "two-up" format as illustrated in FIG. 4. In the cross-section shown in FIG. 4, mechanical fastener 108 is shown in the central portion of fastening laminate 110. First mechanical fastener 108 includes a central zone having no fastening elements although this is not a requirement. Second mechanical fasteners 106a and 106b are positioned toward the edges of the carrier 102 at a distance from the first mechanical fastener 108. Adhesive 104 can be provided at the edges of the carrier for attachment to the backsheet side of an absorbent article while adhesive 104a can be positioned on the second surfaces of second portions 114 of the second mechanical fasteners 106a and 106b for attachment to the topsheet side of an absorbent article. The fastening laminate 110 in the "two-up" format as shown in FIG. 4 can include a line of weakness represented by line 125 in central zone of the first mechanical fastener 108, which has no fastening elements, to facilitate the formation of two separate fastening tabs from the two-up format. Fastening tabs for attachment along both the first and second opposing longitudinal edges of the chassis can be provided from the same laminate roll 110 in this embodiment. Other configurations of the "two-up" format are also possible. Again it may be useful for the laminate in the "two-up" format to be provided in roll form, with optional lines of weakness in the cross-direction as described above.

In the embodiments shown in FIGS. 1, 2A, 2B, 2C, 3, and 4, adhesive is not provided continuously across the entire carrier 2, 102, but only at locations that are attached to the absorbent article and the first and second mechanical fasteners. This can be achieved by pattern coating the carrier 2, 102 with adhesive 4, 4a, 104, 104a. In these embodiments, there is little or no exposed adhesive on the carrier once the fastening laminate is attached to the absorbent article. In some embodiments, adhesive is not used in the fastening laminate at all. Instead, the first mechanical fastener 8, 108 and the first portion 13 of the second mechanical fastener 6, 106a, 106b may be attached to the carrier by other bonding methods (e.g., ultrasonic bonding, thermal bonding, compression bonding, or surface bonding). In other embodiments, the adhesive 4, 104 may be provided as a continuous layer on the carrier 2, 102.

A cross-section of another embodiment of a fastening laminate 210 according to the present disclosure is shown in FIG. 5. The fastening laminate 210 includes a carrier 202 with a continuous layer of adhesive 204 on a first surface of the carrier 202. The first mechanical fastener 208 is attached to the carrier 202 with the adhesive 204 with male fastening elements exposed and extending away from the carrier 202. In the illustrated embodiment, the first mechanical fastener 208 does not extend to the edge of the carrier 202. Film 203, which can be useful as a fingerlift, is positioned at the edge of the carrier 202 at the user's end "U". The second mechanical fastener 206 includes a backing 212 having a first portion 213 and a second portion 214. The backing 212 and consequently each of the first portion 213 and second portion 214 have a first surface 215, and a second surface 216 opposite the first surface 215, with mechanical fastening elements 205 on the first surface 215 of the backing 212 and a layer of adhesive 204a on the second surface 216 of the backing 212. A separate attachment film 209 is attached to the adhesive 204a on the first portion 213 of the second surface 216 of the backing 212 and to the adhesive 204 on the carrier 202 to connect the second mechanical fastener 206 to the carrier 202. In the illustrated embodiment, the same surface of the attachment film 209 is connected to the second mechanical fastener 206 and the carrier 202 making it appear somewhat "S"-shaped although this shape is exaggerated in the drawing. In other embodiments, one surface of the attachment film can be connected to the second mechanical fastener 206 while the opposite surface is attached to the carrier 202. In this embodiment, the attachment film can wrap around the edge of the first portion 213 of the second mechanical fastener 206 in a "C" shape. The second mechanical fastener is positioned such that the first surface and consequently second male fastening elements 205 face the carrier 202. The fastening laminate having attachment films 209 can also be provided in a "two-up" format similar to that shown in FIG. 4. In embodiments of the "two-up" format in which the first mechanical fastener includes a central zone having no fastening elements as shown in FIG. 4, a separate fingerlift film 203 may not be needed.

When a tab of the fastening laminate 210 is attached an absorbent article, a longitudinal edge of the absorbent article can be positioned on the adhesive 204 adjacent attachment film 209 at the manufacturing end "M", and the tab of the fastening laminate 210 can then be folded over the longitudinal edge so that adhesive 204a on the second surface 216 of the backing 212 can attach the tab to the topsheet side of the absorbent article as shown in FIG. 6A. In the illustrated embodiment, to facilitate the removal of the second portion 214 of the second mechanical fastener 206 from the layer of adhesive 204, a non-adhesive film 201 can be positioned between the end of the second mechanical fastener 206 and the adhesive 204 although this is not required in all embodiments.

Referring now to FIG. 6A, the second surface 216 of the backing 212 (shown in FIG. 5) of the second mechanical fastener 206 is attached to the first longitudinal edge 264a of an absorbent article on the topsheet side 261. The carrier 202 is attached to the first longitudinal edge 264a of an absorbent article on the backsheet side 262. In the illustrated embodiment, the second surface 216 of the first portion of the backing 212 remains connected to the carrier through attachment film 209, which wraps around the first longitudinal edge 264a and is attached to the adhesive 204a on the first portion of the second surface 216 of the second mechanical fastener 206 and to the adhesive 204 on the carrier 202. In other embodiments in which one surface of the attachment film is connected to the second mechanical fastener 206 while the opposite surface is attached to the carrier 202, the attachment film may appear somewhat "Z" shaped after the second surface 216 of the second mechanical fastener is attached to the first longitudinal edge 264a of the absorbent article. In either case, the fastening laminate 210 is bonded to the first longitudinal edge 264a of the absorbent article using a Y-bond formed from the carrier 202, the attachment film 209, and the second mechanical fastener 206. As shown in the open configuration of FIG. 6A, there is a separation between the first mechanical fastener 208 and the second mechanical fastener 206 since the first mechanical fastener 208 is outboard from the longitudinal edge 264a of the absorbent article while the second mechanical fastener is positioned at the longitudinal edge. The layer of adhesive 204 is exposed between the first and second mechanical fasteners 206 and 208.

FIG. 6B is a cross-section of the fastening laminate attached to the absorbent article shown in FIG. 6A but configured for storage before use. As illustrated, the fastening tab 210 is folded at the first longitudinal edge 264a such that the first male fastening elements of the first mechanical fastener 208 contact the topsheet side 261 of the chassis. In this configuration, the first male fastening elements of the first mechanical fastener 208 face the topsheet side 261 of the absorbent article and the second male fastening elements 205 of the second mechanical fastener 206 face away from the topsheet side 261 of the absorbent article and toward the carrier 202. Any of the layer of adhesive 204 that may be exposed can be useful to help prevent the fastening laminate from popping open during the manufacturing of the absorbent article, for example. However, we have found that the adhesive 204 in contact with the second male fastening elements 205 advantageously releases from the first surface of the backing sufficiently to allow the fastening tab to be opened readily by the user. It is evident in the illustrated embodiment that the first and second mechanical fasteners 206, 208 do not overlap, but the first male fastening elements of the first mechanical fastener 208 are available to engage with any fibers present on the topsheet side 261 of the absorbent article, which is also useful to help prevent the fastening laminate from popping open.

FIG. 6C is a cross-section of the embodiment shown in FIG. 6A when the front waist region and the rear waist region of the absorbent article overlap to encircle the wearer's waist. This is the configuration of the fastening laminate on the absorbent article while the absorbent article is being worn. In the illustrated embodiment a fibrous material 272 positioned on the backsheet side of the front waist region provides a target area for the first and second mechanical fasteners 206, 208. Advantageously, both the first mechanical fastener 206 and the second mechanical fastener 208 engage with the fibrous material 272, providing secure attachment. In other embodiments, the second mechanical fastener 206 may engage with the backsheet while the first mechanical fastener 208 engages with the fibrous material 272. Also, since the second mechanical fastener 206 is located at the longitudinal edge 264a of the absorbent article, while the first mechanical fastener is outboard from the longitudinal edge 264a of the absorbent article, the fastening laminate according to the present disclosure may resist shifting forces such as torsional or rotational forces caused by movement of the wearer of the absorbent article. In the illustrated embodiment, the layer of adhesive 204 that is exposed between the first and second mechanical fasteners can help provide secure attachment and/or help resist shifting forces caused by movement of the wearer of the absorbent article.

For any of the embodiments of the absorbent article or fastening laminate according to the present disclosure, the fastening laminate can include more than the first and second mechanical fasteners. In some embodiments, the fastening laminate comprises a third mechanical fastener on the first face of the carrier. The third mechanical fastener may be located, for example, at any location between the first and second mechanical fasteners on the first face of the carrier. In some embodiments, the third mechanical fastener and the first mechanical fastener may have separate backings that are abutting, or they may have backings separated by a distance that is usually smaller than the length of each mechanical fastener (that is, in the direction of the longest dimension of the carrier). The first and third mechanical fasteners may be the same or different sizes in either the length or width dimension. An example of a suitable configuration of two fastening patches is described in Int. Pat. Appl. Pub. No. WO 2011/163020 (Hauschildt et al.). In other embodiments, the third mechanical fastener is located sufficiently close to the second mechanical fastener such that when the second mechanical fastener is folded, at least a portion of the second male fastening elements on its second portion abut or are in face-to-face relation with at least some of the male fastening elements on the third mechanical fastener. In some of these embodiments, the second male fastening elements on the second portion of the second mechanical fastener can engage with the male fastening elements on the third mechanical fastener to prevent the laminate from popping open during the manufacturing of the absorbent article, for example. Referring again to FIGS. 5 and 6B, in some embodiments, non-adhesive film 201 can instead be a third mechanical fastener. In some embodiments, there can be one or more strips of mechanical fastener between the first and second mechanical fasteners.

Figure 7:
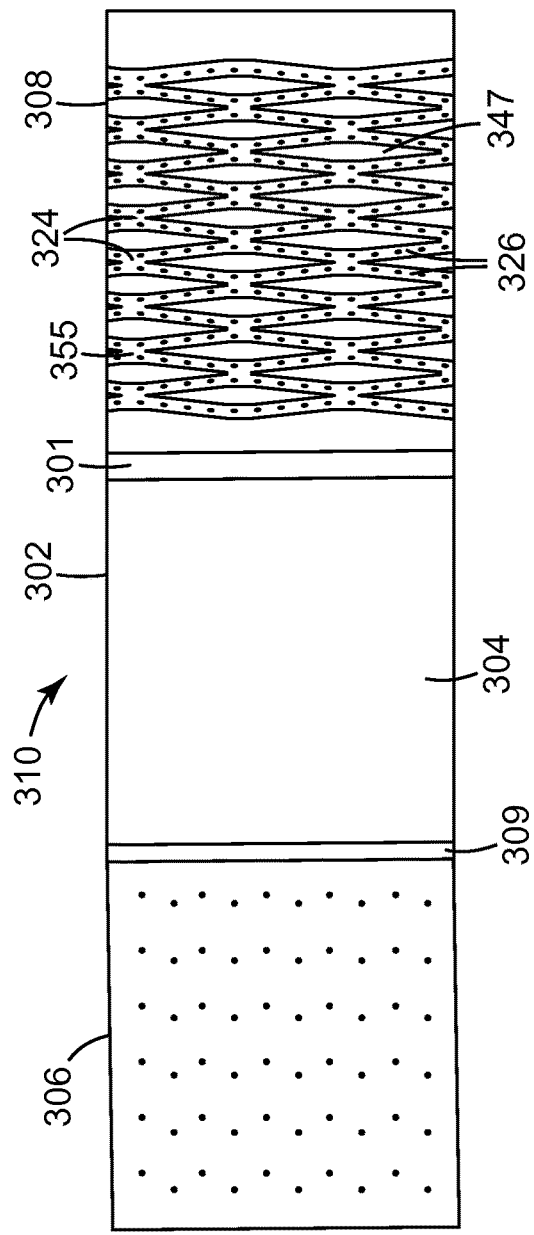
FIG. 7 is a top view of yet another embodiment of a fastening laminate according to the present disclosure.

For any of the embodiments of the absorbent article or fastening laminate according to the present disclosure, including embodiments which incorporate a laminate as shown in FIG. 7, at least one of the first, second, or third mechanical fasteners may include openings 347. FIG. 7 illustrates a top view of fastening laminate 310 according to the present disclosure as it would appear if it were attached to an absorbent article and placed in an open configuration. In FIG. 7, fastening laminate 310 includes first mechanical fastener 308 positioned on the carrier 302. The second mechanical fastener 306 is attached to the carrier 302 with attachment film 309. The fastening laminate 310 also includes a non-adhesive film 301 similar to that in the embodiment shown in FIG. 5.

The first mechanical fastener 308 in the fastening laminate 310 shown in FIG. 7 includes openings therethrough. The openings 347 in first mechanical fastener 308 may be in the form of a repeating pattern of geometric shapes such as polygons. The polygons may be, for example, hexagons or quadrilaterals such as parallelograms or diamonds. The openings 347 may be formed in the first mechanical fastener 308 by any suitable method, including die punching. In some embodiments, the openings may be formed by slitting the thermoplastic backing of a mechanical fastener to form multiple strands 326 attached to each other at intact bridging regions 324 in the backing and separating at least some of the multiple strands 326 between at least some of the bridging regions 324. The bridging regions 324 are regions where the backing is not cut through, and at least a portion of the bridging regions can be considered collinear with the slits. The intact bridging regions 324 of the backing serve to divide the slits into a series of spaced-apart slit portions aligned in the direction of slitting (e.g., the machine direction), which can be referred to as interrupted slits. In some embodiments, for at least some adjacent interrupted slits, the spaced-apart slit portions are staggered in a direction transverse to the slitting direction (e.g., the cross-machine direction). The interrupted slits may be cut into the backing between some pairs of adjacent rows of male fastening elements 355 although this is not a requirement. In some embodiments, curved lines may be used, which can result in crescent shaped openings after spreading. There may be more than one repeating pattern of geometric shaped openings. The openings may be evenly spaced or unevenly spaced as desired. For openings that are evenly spaced, the spacing between the openings may differ by up to 10, 5, 2.5, or 1 percent. Further details about providing openings in a mechanical fastener can be found in U.S. Appl. Pub. No. 2012/0204383 (Wood et al.). In some embodiments, the fastening patch can comprise multiple strands 326 attached to each other at intact bridging regions 324 in the backing without spreading the strands apart to create openings. The interrupted slits may be made in either the longitudinal direction of the absorbent article or in a transverse direction. Such slits may improve the flexibility of the fastening patch and improve the peel performance. Further details about providing interrupted slits in a mechanical fastener can be found in U.S. Appl. Pub. No. 2011/0313389 (Wood et al.).

In some embodiments wherein the first mechanical fastener 308 includes openings 347 (e.g., diamond- or hexagonal-shaped openings), including the embodiment illustrated in FIG. 7, the carrier 302 does not include openings. In some embodiments, the first mechanical fastener 308 and the attachment film 309 are bonded to the carrier 302 with adhesive 304 to form the fastening laminate 310, and the adhesive 304 is exposed in the openings 347. In some embodiments, the adhesive is a pressure sensitive adhesive. The exposed adhesive in the openings 347 is advantageously available to engage the fibers of the absorbent article on the topsheet side, for example, to prevent the fastening laminate 310 from popping open on a manufacturing line for the absorbent article. Typically the portions of exposed adhesive are small enough such that the first mechanical fastener 308 can be released from the absorbent article without requiring excessive force. In other embodiments, adhesive (in some embodiments, pressure sensitive adhesive) is not exposed in the openings 347.

Figure 8:
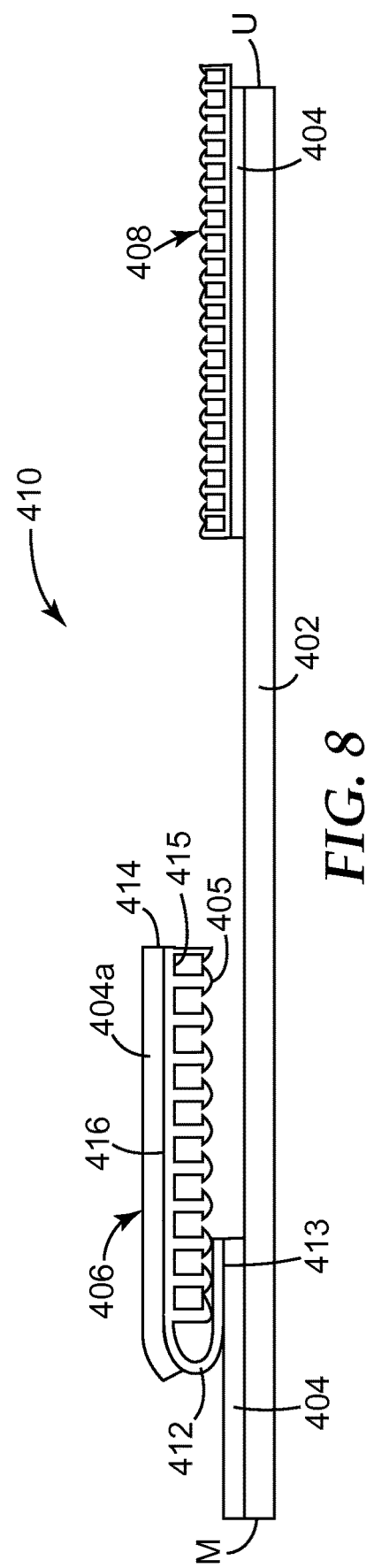
FIG. 8 is a cross-section of still another embodiment of a fastening laminate according to the present disclosure.

A cross-section of another embodiment of a fastening laminate according to the present disclosure is shown in FIG. 8. FIG. 8 shows an example of the fastening laminate as it may look when it is manufactured before it is applied to an absorbent article. Manufacturing end "M" is the end that becomes permanently attached to the absorbent article, and user's end "U" can be releasably attached to the absorbent article during storage or use. The first mechanical fastener 408 is attached toward one end, typically the user's end "U", of the carrier 402 using adhesive 404. The second mechanical fastener 406 is separated from the first mechanical fastener 408. The second surface 416 of the first portion 413 the backing 412 of the second mechanical fastener 406 is attached to the carrier 402. The fastening tab 410 differs from fastening tab 10 shown in FIG. 3, for example, because there are no second male fastening elements on the first portion 413 of the backing 412. The backing 412 of the second mechanical fastener 406 is folded over such that at least part of the first surface 415 of the second portion 414 faces at least part of the first surface 415 of the first portion 413 of the backing 412. The lack of male fastening elements on the first portion 413 of the backing 412 may allow the second mechanical fastener 406 to be folded over easily and may reduce the thickness of the laminate to simplify roll formation. Referring again to FIG. 1, the fastening laminate in the form of fastening tab 410 may be attached to a longitudinal edge 64*a*, 64*b* of an absorbent article 60 by placing the longitudinal edge 64*a*, 64*b* on the adhesive 404 at the manufacturing end "M" of the carrier 402 adjacent the second mechanical fastener 406. The second surface 416 of the second portion 414 of the backing 412 is also provided with adhesive 404*a*. The fastening tab 410 can then be folded over the longitudinal edge 64*a*, 64*b* so that adhesive 404*a* on the second portion 414 of the backing 412 can attach the fastening tab to the topsheet side 61 of the absorbent article as shown in FIG. 2B. While there are no male fastening elements on the first portion 413 of the backing 412, the second male fastening elements 405 on the second portion 414 of the backing 412 located at the longitudinal edge of the absorbent article may serve to resist shifting forces such as torsional or rotational forces caused by movement of the wearer of the absorbent article.

In another embodiment similar to that shown in FIG. 8, the second male fastening elements 405 may be located on the first surface 415 of the first portion 413 of the backing 412 while the second portion 414 of the backing 412 is free of male fastening elements. The length of the first portion 413 and second portion 414 may be adjusted to provide the desired amount of fastening surface for the second mechanical fastener and the desired amount surface for attaching the backing 412 to the absorbent article.

It should be understood that the first and second mechanical fasteners in the fastening laminate and absorbent article according to the present disclosure are separate fasteners, positioned at a distance from each other on the carrier. There is a region between the first and second mechanical fasteners that includes no male fastening elements. In some embodiments, the first and second mechanical fasteners each comprise a backing having a first surface and a second surface opposite the first surface, with male fastening elements on the first surface of the backing, and the backings of the first and second mechanical fasteners are discrete backings. In these embodiments, the first and second mechanical fasteners are connected to the carrier of the fastening laminate at a distance from each other so that a portion of the carrier or, in some embodiments, adhesive, is exposed in between. In some embodiments, the first and second mechanical fasteners share a common backing; that is, the male fastening elements of the first mechanical fastener and the second mechanical fastener have a continuous backing between them. For example, in any of the embodiments illustrated in FIGS. 1, 2A, 2B, 2C, 3, and 4, adhesive 4, 104 can be provided continuously across the carrier 2, 102, and backing 12 may be continuous from second mechanical fastener 6 to first mechanical fastener 8. In these embodiments, the first and second mechanical fasteners readily recognizable as distinct regions having male fastening elements, which are separated by a region free of male fastening elements, and the borders of the first and second mechanical fasteners are determined by the outermost male fastening elements of these regions, not by the backing. In any of these embodiments, the shortest distance between the first mechanical fastener and the first portion of the second mechanical fastener is typically at least as long as the first portion of the second mechanical fastener, which is the portion of the second mechanical fastener attached to the carrier.

In any of the embodiments of the fastening laminate or fastening tab on the absorbent article according to the present disclosure, the first portion of the second mechanical fastener is bonded to the carrier at a position that does not include the edge of the carrier. As described above in connection with fastening laminates 10 and 210 in FIGS. 3 and 5, there is a portion of the carrier 2, 202 adjacent the second mechanical fastener 6, 206 at the manufacturing end "M" that is available to be attached to the backsheet side of the chassis. Thus, the fastening laminates generally have an end portion adjacent the second mechanical fastener that is not covered by a mechanical fastener. In contrast, the first mechanical fastener, which has a surface opposite its male fastening elements bonded to the carrier, may extend to the end of the carrier or beyond.

In the absorbent article according to the present disclosure, the positioning of the second mechanical fastener at the longitudinal edge of the absorbent article and the first mechanical fastener outboard from the longitudinal edge allows the fastening tab disclosed herein to resist shifting forces such as torsional or rotational forces without requiring that the mechanical fastening elements be continuous from inboard the longitudinal edge of the absorbent article to the end of the fastening tab. Thus, good performance can be achieved while offering material cost savings relative to long, continuous mechanical fasteners as shown in U.S. Pat. No. 5,537,722 (Niederhofer).

In any of the embodiments of the fastening laminate and/or the absorbent article according to the present disclosure, to maximize cost savings, the size of first and second mechanical fasteners can be selected such that wherein when the fastening tab is folded at the first longitudinal edge of the absorbent article, the first and second mechanical fasteners do not overlap or mechanically engage. In the laminate, typically the second portion of the second mechanical fastener does not overlap with the first mechanical fastener. In some embodiments, the first and second mechanical fasteners do overlap, but the first mechanical fastener extends beyond the second portion of the second mechanical fastener. In some embodiments, at least about 95%, 90%, 85%, 80%, 75%, 70%, 65%, 60%, 55%, or 50% of the length of the first mechanical fastener (dimension corresponding to the longest dimension of the carrier) does not overlap with the second portion of the second mechanical fastener. Thus, in a storage configuration, the first mechanical fastener is advantageously available to engage with any fibers on the topsheet side of the absorbent article. In some embodiments, the overlap of the first and second portions of the second mechanical fastener can allow the second male fastening elements on these two portions to engage.

In other embodiments, the second mechanical fastener (in some embodiments, the second portion of the second mechanical fastener) overlaps with the first mechanical fastener so that at least about 95%, 90%, 85%, 80%, 75%, 70%, 65%, 60%, 55%, or 50% of the length of the first mechanical fastener (dimension corresponding to the longest dimension of the carrier) is overlapped with the second mechanical fastener. The second mechanical fastener can also be long enough to fully cover the first mechanical fastener and, in the embodiment shown in FIG. 5, can also overlap with the fingerlift film 203. In this embodiment, non-adhesive film 201 can be removed. In some of these embodiments, the second male fastening elements on the second mechanical fastener can engage with the first male fastening elements on the first mechanical fastener. A longer second portion of the second mechanical fastener may be advantageous in the embodiment shown in FIG. 3, for example, to improve roll stability since the resulting laminate could have a more uniform thickness. For example, the thickness of the laminate at the location of the first portion 13 of the backing 12 can be the same as the thickness of the laminate at the location of the first mechanical fastener 8.

Adjusting the length of the second mechanical fastener (in some embodiments, the second portion of the second mechanical fastener) such that it overlaps with the first mechanical fastener can also be useful when there are openings in the first mechanical fastener as shown in FIG. 7, for example. If adhesive is exposed in the openings 347, having the second mechanical fastener extend over at least some of the openings may prevent exposed adhesive in the openings 347 of the first mechanical fastener 308 from adhering too strongly to (and potentially damaging) the topsheet side of the absorbent article when the absorbent article is in the storage configuration, particularly after compression packaging.

In absorbent articles according to the present disclosure, the topsheet is typically permeable to liquid and designed to contact a wearer's skin, and the outwardly facing backsheet is typically impermeable to liquids. There is typically an absorbent core 63 (see FIG. 1) encased between the topsheet and the backsheet. Various materials can be useful for the topsheet, the backsheet, and the absorbent core in an absorbent article according to the present disclosure. Examples of materials useful for topsheets include apertured plastic films, woven fabrics, nonwoven webs, porous foams, and reticulated foams. In some embodiments, the topsheet is a nonwoven material. Examples of suitable nonwoven materials include spunbond or meltblown webs of fiber forming polymer filaments (e.g., polyolefin, polyester, or polyamide filaments) and bonded carded webs of natural polymers (e.g., rayon or cotton fibers) and/or synthetic polymers (e.g., polypropylene or polyester fibers). The nonwoven web can be surface treated with a surfactant or otherwise processed to impart the desired level of wettability and hydrophilicity. The backsheet is sometimes referred to as the outer cover and is the farthest layer from the user. The backsheet functions to prevent body exudates contained in absorbent core from wetting or soiling the wearer's clothing, bedding, or other materials contacting the diaper. The backsheet can be a thermoplastic film (e.g., a poly(ethylene) film). The thermoplastic film may be embossed and/or matte finished to provide a more aesthetically pleasing appearance. The backsheet can also include woven or nonwoven fibrous webs, for example, laminated to the thermoplastic films or constructed or treated to impart a desired level of liquid impermeability even in the absence of a thermoplastic film. Suitable backsheets also include vapor or gas permeable microporous "breathable" materials that are substantially impermeable to liquid. Suitable absorbent cores include natural, synthetic, or modified natural polymers that can absorb and hold liquids (e.g., aqueous liquids). Such polymers can be crosslinked (e.g., by physical entanglement, crystalline domains, covalent bonds, ionic complexes and associations, hydrophilic associations such as hydrogen bonding, and hydrophobic associations or Van der Waals forces) to render them water insoluble but swellable. Such absorbent materials are usually designed to quickly absorb liquids and hold them, usually without release. Examples of suitable absorbent materials useful in absorbent articles disclosed herein include wood pulp or other cellulosic materials and super absorbent polymers (SAP).

In some embodiments of the absorbent article disclosed herein, the absorbent article has ear portions in the rear waist region to which the fastening tabs are attached. For the purposes of the present disclosure, such ear portions are considered part of the chassis. Absorbent articles (e.g., incontinence articles and diapers) according to the present disclosure may have any desired shape such as a rectangular shape, a shape like the letter I, a shape like the letter T, or an hourglass shape. The absorbent article may also be a refastenable pants-style diaper with fastening laminates along each longitudinal edge. In some embodiments, including the embodiment shown in FIG. 1, the topsheet and backsheet are attached to each other and together form the chassis all the way out to the first and second longitudinal opposing edges 64a and 64b. In some of these embodiments, the topsheet and backsheet together form ear portions. In some embodiments, only one of the topsheet or the backsheet extends to the first and second longitudinal opposing edges 64a and 64b. In other embodiments, the chassis can include separate side panels that are attached to the sandwich of at least topsheet, backsheet, and absorbent core during manufacturing of the absorbent article, for example, to form ear portions. The side panels can be made of a material that is the same as the topsheet or backsheet or may be made from a different material (e.g., a different nonwoven). In these embodiments, the side panels also form part of the chassis. In practice, where the fastening tab is joined or otherwise connected to an optional side panel or ear portion, either an extension of the topsheet alone or an extension of the backsheet alone or another separate side panel piece may provide the attachment surfaces the fastening tab. Thus, the second mechanical fastener in the fastening laminate according to the present disclosure can be attached to the topsheet side of the absorbent article without being attached to the topsheet per se. Likewise, the carrier can be attached to the backsheet side of the absorbent article without being attached to the backsheet per se. In any of these embodiments, the absorbent article may comprise an elastic material 69 along at least a portion of first and second longitudinal side edges 64a and 64b to provide leg cuffs.

Referring again to FIG. 1, there is one of the fastening tabs 10 attached to each of the first longitudinal edge 64a and the second longitudinal edge 64b of the chassis in the rear waist region 65. In other embodiments, providing two or more fastening laminates 10 on each of the first and second longitudinal edges 64a and 64b may be advantageous if the absorbent article 60 is relatively large in size (e.g., in an adult incontinence article).

Again referring to FIG. 1, in some embodiments, the first and second mechanical fasteners 6, 8 can engage with a target area 68 comprising a fibrous material 72 arranged on the backsheet 62 of the front waist region 66. For example, loop tapes such as those disclosed in U.S. Pat. No. 5,389,416

(Mody et al.) EP 0,341,993 (Gorman et al.) and EP 0,539,504 (Becker et al.) may be applied to a target area to provide an exposed fibrous material. In other embodiments, the backsheet 62 comprises a woven or nonwoven fibrous layer which is capable of interacting with the first and second fasteners 6, 8. Examples of such backsheets 62 are disclosed, for example, in U.S. Pat. No. 6,190,758 (Stopper) and U.S. Pat. No. 6,075,179 (McCormack et al.). In these embodiments, the first and second mechanical fasteners 6, 8 advantageously may engage with any suitable location on the backsheet, which can be determined by the size of the wearer and the desired fit. Furthermore, with the multiple mechanical fasteners in the fastening laminate according to the present disclosure, adequate fastening between the first and second mechanical fasteners 6, 8 and the backsheet 62 may be possible, allowing the use of a smaller target area 68 or the elimination of target area 68 altogether, which offers further material cost savings.

The fastening laminate according to the present disclosure and the absorbent articles that contain them include a carrier 2, 102, 202, 302, 402. The carrier 2, 102, 202, 302, 402 may be continuous (i.e., without any through-penetrating holes) or discontinuous (e.g. comprising through-penetrating perforations or pores). The carrier 2, 102, 202, 302, 402 may comprise a variety of suitable materials including woven webs, non-woven webs (e.g., spunbond webs, spunlaced webs, airlaid webs, meltblown web, and bonded carded webs), textiles, paper, plastic films (e.g., single- or multi-layered films, coextruded films, laterally laminated films, or films comprising foam layers), and combinations thereof. In some embodiments, the carrier is a fibrous material (e.g., a woven, nonwoven, or knit material). In some embodiments, the carrier comprises a nonwoven. The term "nonwoven" when referring to a carrier or web means having a structure of individual fibers or threads which are interlaid, but not in an identifiable manner as in a knitted fabric. Nonwoven fabrics or webs can be formed from various processes such as meltblowing processes, spunbonding processes, spunlacing processes, and bonded carded web processes. In some embodiments, the carrier comprises multiple layers of nonwoven materials with, for example, at least one layer of a meltblown nonwoven and at least one layer of a spunbonded nonwoven, or any other suitable combination of nonwoven materials. For example, the carrier may be a spunbond-meltbond-spunbond, spunbond-spunbond, or spunbond-spunbond-spunbond multilayer material. Or, the carrier may be a composite web comprising a nonwoven layer and a dense film layer (e.g., a thermoplastic film layer) or a composite web comprising one or more laterally laminated film portions and nonwoven portions. The carrier may be provided with a release coating (e.g., a silicone, fluorochemical, or carbamate coating) on its second surface (opposite the first surface to which the first and second mechanical fasteners are applied) when adhesives are used to join the components of the fastening laminate according to the present disclosure.

Fibrous materials that can provide useful carriers 2, 102, 202, 302, 402 may be made of natural fibers (e.g., wood or cotton fibers), synthetic fibers (e.g., thermoplastic fibers), or a combination of natural and synthetic fibers. Examples of suitable materials for forming thermoplastic fibers include polyolefins (e.g., polyethylene, polypropylene, polybutylene, ethylene copolymers, propylene copolymers, butylene copolymers, and copolymers and blends of these polymers), polyesters, and polyamides. The fibers may also be multi-component fibers, for example, having a core of one thermoplastic material and a sheath of another thermoplastic material. Useful carriers 2, 102, 202, 302 may have any suitable basis weight or thickness that is desired for a particular application. For a fibrous carrier, the basis weight may range, e.g., from at least about 5, 8, 10, 20, 30, or 40 grams per square meter, up to about 400, 200, 100, or 50 grams per square meter. The carrier may be up to about 5 mm, about 2 mm, or about 1 mm in thickness and/or at least about 0.1, about 0.2, or about 0.5 mm in thickness.

In some embodiments of the fastening laminate according to the present disclosure and the absorbent articles that contain them, one or more zones of the carrier 2, 102, 202, 302, 402 may comprise one or more elastically extensible materials extending in at least one direction when a force is applied and returning to approximately their original dimension after the force is removed. However, in some embodiments, at least the portion of the carrier joined to the fastening patch is not stretchable or has up to a 10 (in some embodiments, up to 9, 8, 7, 6, or 5) percent elongation in the CD.

The size of the carrier in the fastening tab described herein may be such that it is suitable for the desired size of the absorbent article. In some embodiments, for example, when the fastening tab is useful for an adult incontinence article, the carrier has a length in a range from 50 millimeters to 80 millimeters and a width in a range from 15 millimeters to 40 millimeters. In some of these embodiments, the carrier has a length in a range from 55 millimeters to 70 millimeters and a width in a range from 25 millimeters to 30 millimeters. In some embodiments, when the laminate is useful for a baby diaper, the carrier has a length in a range from 25 millimeters to 60 millimeters and a width in a range from 10 millimeters to 30 millimeters.

In any of the embodiments of the fastening laminate and/or absorbent article according to the present disclosure, the first and second mechanical fasteners typically have male fastening elements on a backing. The backing and the male fastening elements are typically integral (that is, formed at the same time as a unit, unitary). First and second mechanical fasteners are typically made from at least one thermoplastic material. Suitable thermoplastic materials for mechanical fasteners include polyolefin homopolymers such as polyethylene and polypropylene, copolymers of ethylene, propylene and/or butylene; copolymers containing ethylene such as ethylene vinyl acetate and ethylene acrylic acid; polyesters such as poly(ethylene terephthalate), polyethylene butyrate and polyethylene naphthalate; polyamides such as poly(hexamethylene adipamide); polyurethanes; polycarbonates; poly(vinyl alcohol); ketones such as polyetheretherketone; polyphenylene sulfide; and mixtures thereof. Typically, the thermoplastic is a polyolefin (e.g., polyethylene, polypropylene, polybutylene, ethylene copolymers, propylene copolymers, butylene copolymers, and copolymers and blends of these materials).

Male fastening elements on a backing can be made, for example, by feeding a thermoplastic material onto a continuously moving mold surface with cavities having the inverse shape of the posts. The thermoplastic material can be passed between a nip formed by two rolls or a nip between a die face and roll surface, with at least one of the rolls having the cavities. The cavities may be in the inverse shape of a capped post having a loop-engaging head or may be in the inverse shape of a post without loop-engaging heads (e.g., a precursor to a male fastening element). Pressure provided by the nip forces the resin into the cavities. In some embodiments, a vacuum can be used to evacuate the cavities for easier filling of the cavities. The nip typically has a large enough gap such that a coherent backing is formed over the cavities. The mold surface and cavities can optionally be air or water cooled before stripping the integrally formed backing and upstanding hook elements from the mold surface such as by a stripper roll. If the posts formed upon exiting the cavities do not have loop-engaging heads, loop-engaging heads could be subsequently formed into hooks by a capping method as described in U.S. Pat. No. 5,077,870 (Melbye et al.). Typically, the capping method includes deforming the tip portions of the hook elements using heat and/or pressure. The heat and pressure, if both are used, could be applied sequentially or simultaneously.

Suitable tool rolls include those formed from a series of plates defining a plurality of post-forming cavities about its periphery such as those described, for example, in U.S. Pat. No. 4,775,310 (Fischer). Cavities may be formed in the plates by drilling or photoresist technology, for example. Other suitable tool rolls may include wire-wrapped rolls, which are disclosed along with their method of manufacturing, for example, in U.S. Pat. No. 6,190,594 (Gorman et al.). Another exemplary method for forming a thermoplastic backing with upstanding posts includes using a flexible mold belt defining an array of upstanding post-shaped cavities as described in U.S. Pat. No. 7,214,334 (Jens et al.). Yet other useful methods for forming a thermoplastic backing with upstanding posts can be found in U.S. Pat. No. 6,287,665 (Hammer), U.S. Pat. No. 7,198,743 (Tuma), and U.S. Pat. No. 6,627,133 (Tuma).

Another method for forming a thermoplastic backing with upstanding male fastening elements is profile extrusion, which is described, for example, in U.S. Pat. No. 4,894,060 (Nestegard). Typically, in this method a thermoplastic flow stream is passed through a patterned die lip (e.g., cut by electron discharge machining) to form a web having downweb ridges. The ridges can then be transversely sliced at spaced locations along the extension of the ridges to form upstanding fastening elements with a small separation caused by the cutting blade. The separation between upstanding fastening elements is then increased by stretching.

The male fastening elements on the mechanical fasteners of the fastening laminate and absorbent articles disclosed herein typically have loop-engaging heads that have an overhang. The term "loop-engaging" as used herein relates to the ability of a male fastening element to be mechanically attached to a loop material. Suitable male fastening elements with loop-engaging heads can have any desired shape. For example, the male fastening element may be in the shape of a mushroom (e.g., with a circular or oval head enlarged with respect to the stem), a hook, a palm-tree, a nail, a T, or a J. The loop-engageability of male fastening elements may be determined and defined by using standard woven, nonwoven, or knit materials. A region of male fastening elements with loop-engaging heads generally will provide, in combination with a loop material, at least one of a higher peel strength, higher dynamic shear strength, or higher dynamic friction than a region of posts without loop-engaging heads. Typically, male fastening elements that have loop-engaging heads have a maximum thickness dimension (in either dimension normal to the height) of up to about 1 (in some embodiments, 0.9, 0.8, 0.7, 0.6, 0.5, or 0.45) millimeter.

The male fastening elements on the mechanical fasteners of the laminate and absorbent articles disclosed herein can have a variety of useful maximum heights (above the backing) of up to 3 mm, 1.5 mm, 1 mm, or 0.5 mm and, in some embodiments a minimum height of at least 0.05 mm, 0.1 mm, or 0.2 mm. The upstanding posts have a variety of aspect ratios (that is, a ratio of height to width at the widest point) such as at least about 2:1, 3:1, or 4:1. Advantageously, a variety of densities of the upstanding fastening elements may be useful. For example, the male fastening elements have a density of at least 248 per square centimeter ($cm^2$) (1600 per square inch, $in^2$) and up to about 1500/$cm^2$ (10000/$in^2$), 1240/$cm^2$ (8000/$in^2$), or 852/$cm^2$ (5500/$in^2$). For example, the density of the male fastening elements may be in a range from 271/$cm^2$ (1750/$in^2$) to about 852/$cm^2$ (5500/$in^2$) or from 248/$cm^2$ (1600/$in^2$) to 542/$cm^2$ (3500/$in^2$). The spacing of the male fastening elements need not be uniform.

In some embodiments, the thickness of the backing of the first and/or second mechanical fasteners 6, 8, 106, 108, 206, 208, 306, 406, 308, 408 described herein may be up to about 400, 250, 150, 100, 75 or 50 micrometers, which does not include the height of male mechanical fastening elements on the surface of the backing. In some embodiments, the thickness of the backing is in a range from 30 to about 225 micrometers, from about 50 to about 200 micrometers, or from about 100 to about 150 micrometers.

Although identical mechanical fasteners can be used for the first and second mechanical fasteners, in some embodiments, the second mechanical fastener is different from the first mechanical fastener. In some embodiments of the fastening laminate and absorbent article according to the present disclosure, including the embodiments shown in FIGS. 2A, 2B, 2C, 3, 4, and 8, it may be useful for the second mechanical fastener 6, 106a, 106b, 206, 306, 406 to have a relatively thin backing 12. A relatively thin backing 12 may be useful in the embodiments shown in FIGS. 2A, 2B, 2C, 3, 4, and 8 to facilitate the folding over of the backing 12, for example, during the manufacturing of the laminate. Since the second mechanical fastener is at the longitudinal edge 64a of the absorbent article 60 shown in FIG. 1, it may be more likely to come into contact with the skin of the wearer than the first mechanical fastener 8. A mechanical fastener with a relatively thin backing 12 may be more skin-friendly than a mechanical fastener with a thicker backing. The thickness of the backing 12 of the second mechanical fastener 6 may be in a range from 20 µm to 80 µm, in some embodiments, in a range from 20 µm to 70 µm or 30 µm to 70 µm. Relatively thin backings having such thicknesses, for example, are also useful in embodiments in which the first mechanical fastener and the second mechanical fastener share a common backing. The thickness of the backing may be controlled by the gap in the nip described above in the method of making a mechanical fastener. Reducing the thickness of the backing can also be achieved by stretching the backing, for example, after formation of upstanding posts. In these embodiments, the backing has stretch-induced molecular orientation.

In some embodiments, the second male fastening elements are different from the first male fastening elements. Because of the positions of the first and second mechanical fasteners on the absorbent article, the second male fastening elements on the second mechanical fasteners may also be selected based primarily on shear performance, while peel performance may be more important for the first male fastening elements on the first mechanical fasteners. Accordingly, the second male fastening elements on the second mechanical fasteners may have smaller heads than those on the first mechanical fasteners or may have no heads at all. In other embodiments, the second male fastening elements may be selected based on skin friendliness while the first male fastening elements may be based on shear and peel performance. The density of the upstanding fastening elements and the cap area may be used to determine a relative cap density in the mechanical fastener disclosed herein. The relative cap density, which is sometimes referred to as an aspect ratio, can affect the feel of the mechanical fastener when the upstanding fastening elements come into contact with a person's skin. The relative cap density is a measurement of the aggregate cap area divided by the overall area of the mechanical fastener. In some embodiments of the mechanical fasteners disclosed herein, (in some embodiments, the second mechanical fastener) relative cap density is in a range from 10 percent to 40 percent, and, in some embodiments, 10 percent to 30 percent, 15 percent to 30 percent, or 10 percent to 24 percent.

For fastening laminates and absorbent articles according to the present disclosure, the first and second mechanical fasteners 6, 8 may be joined to the carrier 2, for example, by lamination (e.g., extrusion lamination), adhesives (e.g., pressure sensitive adhesives, hot melt adhesives, or structural adhesives), or other bonding methods (e.g., ultrasonic bonding, thermal bonding, compression bonding, or surface bonding). In the illustrated embodiments, a layer of adhesive 4, 104, 204, 304, 404, is used to join the first and second mechanical fasteners 6, 106a, 106b, 206, 306, 406, 8, 108, 208, 308, 408 to the carrier 2, 102, 202, 302, 402. In any of the embodiments of the fastening laminate and absorbent article according to the present disclosure, the adhesive is generally made up of an adhesive having a peel strength that is sufficient to permanently attach the first and second mechanical fasteners 6, 106a, 106b, 206, 306, 406, 8, 108, 208, 308, 408 to the carrier 2, 102, 202, 302, 402. The adhesive used may be any conventional adhesive, including pressure sensitive adhesives (PSAs) and non-pressure sensitive adhesives. PSAs are well known to those of ordinary skill in the art to possess properties including the following: (1) aggressive and permanent tack, (2) adherence with no more than finger pressure, (3) sufficient ability to hold onto an adherend, and (4) sufficient cohesive strength to be cleanly removable from the adherend. Materials that have been found to function well as PSAs are polymers designed and formulated to exhibit the requisite viscoelastic properties resulting in a desired balance of tack, peel adhesion, and shear holding power. Suitable pressure sensitive adhesives include acrylic resin and natural or synthetic rubber-based adhesives and may be hot melt pressure sensitive adhesives. Illustrative rubber based adhesives include styrene-isoprene-styrene, styrene-butadiene-styrene, styrene-ethylene/butylenes-styrene, and styrene-ethylene/propylene-styrene that may optionally contain diblock components such as styrene isoprene and styrene butadiene. The adhesive may be applied using hot-melt, solvent, or emulsion techniques.

In some embodiments, the first mechanical fastener and the first portion of the second surface of the backing of the second mechanical fastener is directly bonded to the carrier non-adhesively. In some embodiments the first and second mechanical fasteners 6, 106a, 106b, 206, 306, 406, 8, 108, 208, 308, 408 are joined to the carrier 2, 102, 202, 302, 402 using surface bonding or loft-retaining bonding techniques. The term "surface-bonded" when referring to the bonding of fibrous materials means that parts of fiber surfaces of at least portions of fibers are melt-bonded to the backing of the mechanical fastener, on a side opposite the male fastening elements, in such a manner as to substantially preserve the original (pre-bonded) shape of the surface of the backing and to substantially preserve at least some portions of the surface of the backing in an exposed condition in the surface-bonded area. Quantitatively, surface-bonded fibers may be distinguished from embedded fibers in that at least about 65% of the surface area of the surface-bonded fiber is visible above the surface of the backing in the bonded portion of the fiber. Inspection from more than one angle may be necessary to visualize the entirety of the surface area of the fiber. The term "loft-retaining bond" when referring to the bonding of fibrous materials means a bonded fibrous material comprises a loft that is at least 80% of the loft exhibited by the material prior to, or in the absence of, the bonding process. The loft of a fibrous material as used herein is the ratio of the total volume occupied by the web (including fibers as well as interstitial spaces of the material that are not occupied by fibers) to the volume occupied by the material of the fibers alone. If only a portion of a fibrous web has the surface of the backing bonded thereto, the retained loft can be easily ascertained by comparing the loft of the fibrous web in the bonded area to that of the web in an unbonded area. It may be convenient in some circumstances to compare the loft of the bonded web to that of a sample of the same web before being bonded. In some of these embodiments, joining the first and/or second mechanical fastener to a fibrous carrier comprises impinging heated gaseous fluid (e.g., ambient air, dehumidified air, nitrogen, an inert gas, or other gas mixture) onto a first surface of the fibrous web carrier while it is moving; impinging heated fluid onto the second surface of the backing while the continuous web is moving, wherein the second surface is opposite the male fastening elements; and contacting the first surface of the fibrous web with the second surface of the backing so that the first surface of the fibrous web is melt-bonded (e.g., surface-bonded or bonded with a loft-retaining bond) to the second surface of the backing. Impinging heated gaseous fluid onto the first surface of the fibrous web and impinging heated gaseous fluid on the second surface of the backing may be carried out sequentially or simultaneously. Further methods and apparatus for joining a continuous web to a fibrous carrier web using heated gaseous fluid may be found in U.S. Pat. Appl. Pub. Nos. 2011/0151171 (Biegler et al.) and 2011/0147475 (Biegler et al.).

Other components of the fastening laminate according to the present disclosure, such as the non-adhesive film 201, fingerlift film 203, and attachment film 209 shown in FIGS. 5 and 6A to 6C can be made of cloth, kraft paper, cellophane film, nonwoven webs, polymeric films (e.g., polypropylene, polyethylene terephthalate, and polyethylene) or other suitable materials or laminates. Also, any of the materials described above as suitable for the carrier may be useful for the non-adhesive film, fingerlift film, and attachment film.

The method according to the present disclosure includes providing a chassis and a fastening tab and attaching the fastening tab to the chassis. The chassis has a topsheet side, a backsheet side, and first and second opposing longitudinal edges extending from a rear waist region to an opposing front waist region. The fastening tab includes at least a carrier and a first mechanical fastener having first male fastening elements, the first mechanical fastener disposed on the carrier. In some embodiments, the fastening tab includes a second mechanical fastener that includes a backing having a first surface and a second surface opposite the first surface, with second male fastening elements on the first surface of the backing. A first portion of the second surface of the backing is connected to the carrier. Attaching the fastening tab to the chassis includes connecting a second portion of the second surface of the backing to the first longitudinal edge of the chassis on the topsheet side, and attaching the carrier to the first longitudinal edge of the chassis on the backsheet side. Typically the fastening tab is attached to the first longitudinal edge of the chassis in the rear waist region. The fastening tab may be provided from a fastening laminate according to any of the embodiments of the fastening laminate described above. In some embodiments, the fastening tab is provided from a roll of a laminate including first and second fastening strips on the first face of the carrier web. In these embodiments, attaching the second mechanical fastener to the carrier typically precedes attaching the second mechanical fastener to the first longitudinal edge of the chassis on the topsheet side. In other embodiments, the second mechanical fastener may simultaneously be attached to the carrier and to the first longitudinal edge of the chassis on the topsheet side. That is, the fastening laminate as manufactured for use in the method disclosed herein need not include the second mechanical fastener.

In the absorbent article and method according to the present disclosure, the fastening laminate according to the present disclosure is attached to the chassis of the absorbent article. Referring again to FIG. 1, the fastening tab 10 may be attached to the longitudinal edge 64a of the absorbent article 60 using any suitable method. For example, adhesives (e.g., pressure sensitive adhesives, hot melt adhesives, or structural adhesives), non-adhesive bonding (e.g., ultrasonic bonding, thermal bonding, compression bonding, or surface bonding as described above), or a combination of any of these methods may be useful. In the embodiments illustrated herein, the fastening tab 10, 210, 310, 410 is attached to the longitudinal edge 64a, 264a of the absorbent article 60 using adhesive 4, 4a, 204, 204a, 304, 404, 404a.

For the method of making an absorbent article according to the present disclosure, conveniently, it may be useful to provide a continuous web of a plurality of chassis including the absorbent core encased between the topsheet and the backsheet. The chassis in the continuous web may have any shape or construction as described above in connection with FIG. 1.

Advantageously, laminates useful for the absorbent articles according to the present disclosure can be handled with conventional diaper- or incontinence article-manufacturing equipment. For example, the laminates are provided and fed to a continuous web of a plurality of chassis by one or more vacuum wheel applicators. A laminate roll can be cut with a pinch cut knife and anvil. Also, a paddle wheel apparatus can be used where a laminate roll is extruded through a window knife and shear cut by a rotating fly knife. Conventional manufacturing equipment for absorbent articles further includes glue-in-line capability as well as ultrasonic or thermal bonding equipment, any of which may be useful, alone or in combination, to attach the laminate to the chassis.

In some embodiments of the method according to the present disclosure, at least one of the first, second, or third mechanical fasteners includes openings. In some embodiments, the openings may be formed by slitting the thermoplastic backing of a mechanical fastener to form multiple strands 326 attached to each other at intact bridging regions 324 in the backing and separating at least some of the multiple strands 326 between at least some of the bridging regions 324 as described above in connection with FIG. 7. Slit webs typically develop little to no stress in the direction of spreading at least upon initially straining the slit web in the spreading direction. The stress can be affected by the size of the slits in a slit web. The slits provide regions where any means for transmission of force in the spreading direction is substantially absent. Accordingly, for any of the embodiments of the method according to the present disclosure in which the first and/or the second mechanical fasteners include the backing with openings formed by strands of the backing attached to each other at intact bridging regions in the backing and separated from each other between the bridging regions, spreading the slit mechanical fastener to provide multiple strands separated from each other between at least some of the bridging regions to provide openings can be carried out in a variety of suitable ways. When spreading is desired in the machine direction of a continuous web (e.g., with interrupted slits are made in the cross-web direction), monoaxial spreading in the machine direction can be performed by propelling the thermoplastic web over rolls of increasing speed, with the downweb roll speed faster than the upweb roll speed. When spreading is desired in a cross-direction or other angle to the machine direction, spreading can be carried out on a continuous web using a flat film tenter apparatus, diverging rails, diverging disks, or a series of bowed rollers. A method of using diverging disks for spreading a slit web is described in Int. Pat. App. Pub. No. WO 2013/172957 (Gilbert et al.). When the first and/or second mechanical fasteners in the laminates disclosed herein are provided by a mechanical fastening patch cut to a desired size, spreading the slit mechanical fastener may also be carried out, for example, by hand.

In a web process for providing first and/or the second mechanical fasteners that include the backing with openings formed by strands of the backing attached to each other at intact bridging regions in the backing and separated from each other between the bridging regions, it may be useful to spread a slit web in the cross-machine direction by moving the slit web over a crowned surface. A crowned surface can be considered any forming surface that lengthens the path of a portion of the slit web. Useful crowned surfaces have a varying height dimension in a direction corresponding to the CD of the slit web. Generally, the height of the crowned surface is greatest at its center. The crowned surface may be a smooth surface having a generally spherical or elliptical shape in which the diameter or axis continuously increases toward its center, but a useful crowned surface need not have a uniform height variation over its entire portion that contacts the slit web. For example, the crown surface may have a flat portion where the slit web first contacts it, and the curvature of the crowned surface in a direction corresponding to the CD of the slit web may increase in the direction of the slit web path. The crowned surface may also have, in some embodiments, ridges or other surface irregularities.

Any surface over which a web in tension is bent or wrapped around is believed to impart a force on the web that is normal or perpendicular to the web. Because of the varying height of a crowned surface, the force imparted on a web by a crowned surface is not evenly distributed. Without wanting to be bound by theory, it is believed that the crowned surface can spread open a slit web as described herein because a component of the normal force generated by a crowned surface will be in the cross-web direction. The cross-direction strength of the web is relatively low because of the slits in the web, and the amount of tension in the web that would resist spreading is low. Therefore, the cross-directional component of the force generated by a crowned surface can induce spreading of a slit web.

The amount of spreading that can result by moving a slit web over a crowned surface can be limited by the frictional force resisting the cross-directional movement of the spreading web. Because of this, it may be desirable to minimize the friction between the slit web and the crowned surface. Such friction can be decreased if at least a portion of the crowned surface is a low-friction surface. For example, a least a portion of the crowned surface can be made from a low-friction material or can be coated with a low-friction coating.

Also, if the crowned surface is an air bearing, friction between the slit web and the crowned surface may be decreased. Since the coefficient of kinetic friction of two materials is generally lower than the corresponding coefficient of static friction, it is typically desirable that the crowned surface and the slit web are not moving at the same speed in the same direction so that the crowned surface and the slit web can have a "slipping" interface. Accordingly, in some cases, the crowned surface does not rotate, or, in other words, it is stationary. Further information regarding a spreading a slit web using a crowned surface can be found in Int. Pat. App. Pub. No. WO 2013/172960 (Gilbert et al.).

Another web process for providing first and/or the second mechanical fasteners having the backing with openings formed by strands of the backing attached to each other at intact bridging regions in the backing and separated from each other between the bridging regions includes running a slit web in the machine direction onto a stretchable surface. The slit web is in contact with the stretchable surface for a path length in the machine direction, and for at least a portion of the path length, the stretchable surface is stretching in the cross-machine direction. The traction between the slit web and the stretchable surface during the stretching at least partially separates at least some of the multiple strands of the slit web in a second direction transverse to the first direction. In some cases, the slit web is run over a roller comprising two rotating diverging disks that are laterally spaced and have the stretchable surface between them that stretches in the cross-machine direction for a portion of a rotation of the two rotating diverging disks. The stretchable surface stretches for 180 degrees of the rotation of the diverging disks as it moves from the position where the disks are closest together to the position where the disks are farthest apart. The band then retracts for 180 degrees of the rotation of the diverging disks as it moves from the position where the disks are farthest apart to the position where the disks are closest together. Multiple strands of a slit web that come into contact with the stretchable surface at any position where the stretchable surface is stretching will be spread apart in the direction of the stretch. The slit web may be positioned to be in contact with the stretchable surface for any portion of the rotation sufficient to at least partially separate at least some of the multiple strands of the slit web. The angle of the diverging disks can be selected depending on the desired amount of spread in the slit web. For example, each diverging disk may independently be angled at least 1, 2, 3, 4, or 5 degrees and up to 20, 15, or 10 degrees with respect to the machine direction of the running web. In some embodiments, each diverging disk is independently angled in a range from 1 to 10 degrees or 2.5 to 7.5 degrees. Since the diverging disks may be independently angled, the method according to the present disclosure may be useful for spreading the slit web uniformly or non-uniformly with respect to the center of the slit web. In some embodiments, the strands closer to one edge of the slit web may be spread apart more than the strands closer to the opposite edge of the slit web.

A variety of materials can be useful as stretchable surfaces. For examples, elastic bands, elastic tubing, coiled springs, or an elastic sleeve may be useful and may be attached to the diverging disks by pins, clamps, belts, or any other of a variety of useful methods. The term "elastic" refers to any material (such as a film that is 0.002 mm to 0.5 mm thick) that exhibits recovery from stretching or deformation. In some embodiments, a material may be considered to be elastic if, upon application of a stretching force, it can be stretched to a length that is at least about 25 (in some embodiments, 50) percent larger than its initial length and can recover at least 40, 50, 60, 70, 80, or 90 percent of its elongation upon release of the stretching force. Typically, elastic materials are considered "high-friction" materials and may allow for sufficient traction between the slit web and the stretching surface so that the slit web spreads apart along with the stretching surface. A particular elastic material may be selected for the stretching surface to maximize the traction with the slit web. It may also be useful to increase the traction between a given stretching surface and a slit web, for example, by increasing the machine direction tension on the web or by providing the stretching surface with surface structure (e.g., microstructures). In embodiments in which the slit web includes male fastening elements comprising upstanding posts having bases attached to the slit web, the upstanding posts can be directed to face against the stretching surface, which may be a structured surface, to increase traction. When the stretching surface is a coiled spring, the coiled spring may be metal (e.g., aluminum or steel) and may be coated with a high-friction coating, if desired. The high-friction coating can be, for example, a coating of an elastomeric material or a plasma coating known to provide a high-friction surface. Different types of stretchable surfaces may be useful together to provide different advantageous properties, for example, elongation, stiffness, or friction properties. Further information regarding a spreading a slit web using a stretchable surface can be found in U.S. Pat. App. Pub. No. 2014/0332999 (Rothwell et al.).

When separating strands of a web including interrupted slits, it is typically advantageous to not allow the attached multiple strands of the spread web to twist out-of-plane. Twisted strands of the spread web create a non-uniform contact surface, which can complicate heat transfer to the web and complicate the use of a nip in further web processing (e.g., annealing or laminating as described below) since the twisted strands may be crushed by the nip. In a web process, tension applied in the machine direction, which exerts a force normal to the slit web, can be adjusted to keep the attached strands in plane. Also, adjusting the amount of spreading (e.g., using the geometry of a crowned surface or the angle of diverging disks) can also control out-of-plane twisting.

In some embodiments, the first or second mechanical fastener in the form of a spread mechanical fastening web is annealed before it is attached to the carrier with the adhesive layer. In some embodiments, annealing comprises heating the spread web. In some embodiments, annealing comprises heating and then cooling (e.g., rapidly cooling) the spread web to maintain its configuration. Heating and/or annealing can be carried out, for example, after the spread web has been spread to the final desired extent or at an intermediate stage, for example, if the spread web is spread a second time with a second stretchable surface. Annealing the spread web can be useful, for example, depending on the extent of spreading, and can be useful to maintain the openings between multiple strands, for example, when the width of the slit web has been increased by at least 50 percent. Annealing can also be useful, for example, for maintaining at least some of the multiple strands in a substantially coplanar arrangement. In some embodiments, heating is only applied to the second surface of the spread mechanical fastening web (i.e., the surface opposite the first surface from which the mechanical fastening elements project) to minimize any damage to the mechanical fastening elements that may result from heating. Heating may be accomplished, for example, using heated rollers after the slit web is spread.

Non-contact heating methods such as IR irradiation, hot air treatment, or by directing the web through a heated chamber may also be useful. It may also be useful, in some embodiments, to heat the slit web before it is spread using any of these heating methods.

Whether or not (or before or after) a spread mechanical fastening web is annealed, the spread web may be handled by a high-friction roller (e.g., comprising an elastomeric material as described above or a material with a rough surface). The high-friction roller may be heated or chilled, if desired, or may be useful at room temperature. A high-friction roller may be useful, for example, for holding the spread web in a spread configuration whether or not the web is annealed. In some embodiments, a heated, high-friction roller may be useful for annealing the spread web.

In some cases, the spread mechanical fastening web may be in the form of a roll. The bridging regions interrupting the interrupted slits allow the spread web to be handled as an integral unit, for example, to be handled in roll form and converted as desired, for example, before it is laminated to the carrier.

The fastening laminates according to the present disclosure are also useful for other articles such as smocks, hospital gowns, caps, other incontinent garments, and other absorbent articles, e.g., sanitary napkins.

Some Embodiments of the Disclosure

In a first embodiment, the present disclosure provides an absorbent article comprising:
 a chassis with a topsheet side, a backsheet side, and first and second opposing longitudinal edges extending from a rear waist region to an opposing front waist region; and
 a fastening tab comprising a carrier, a first mechanical fastener having first male fastening elements, the first mechanical fastener disposed on the carrier, and a second mechanical fastener, wherein the second mechanical fastener comprises a backing having a first surface and a second surface opposite the first surface, wherein for a first portion of the backing, the second surface of the backing is connected to the carrier, wherein for a second portion of the backing, the second surface of the backing is attached to the first longitudinal edge of the chassis on the topsheet side, wherein the carrier is attached to the first longitudinal edge of the chassis on the backsheet side, and wherein for at least one of the first portion or second portion of the backing, second male fastening elements are disposed on the first surface of the backing. It should be understood that there is a region between the first mechanical fastener and second mechanical fastener that does not include male fastening elements.

In a second embodiment, the present disclosure provides the absorbent article of the first embodiment, wherein the first portion of the second surface of the backing is adhesively attached to the carrier.

In a third embodiment, the present disclosure provides the absorbent article of the first or second embodiment, wherein the second male fastening elements are disposed on the first surface of both the first portion and the second portion of the backing, wherein when the fastening tab is folded at the first longitudinal edge such that the first male fastening elements of the first mechanical fastener contact the topsheet side of the chassis, at least some of the second male fastening elements on the first surface of the first portion of the backing abut at least some of the second male fastening elements on the first surface of the second portion of the backing.

In a fourth embodiment, the present disclosure provides the absorbent article of the third embodiment, wherein at least some of the second male fastening elements on the first portion of the first surface of the backing mechanically engage with at least some of the second male fastening elements on the second portion of the first surface of the backing.

In a fifth embodiment, the present disclosure provides the absorbent article of the first embodiment, wherein the second surface of the first portion of the backing is connected to the carrier using an attachment film.

In a sixth embodiment, the present disclosure provides the absorbent article of the fifth embodiment, wherein the attachment film is adhesively attached to a first portion of the second surface of the backing and to the carrier.

In a seventh embodiment, the present disclosure provides the absorbent article of the sixth embodiment, wherein the attachment film wraps around the first longitudinal edge of the chassis.

In an eighth embodiment, the present disclosure provides the absorbent article of any one of the first to seventh embodiments, wherein when the fastening tab is folded at the first longitudinal edge such that the first male fastening elements of the first mechanical fastener contact the topsheet side of the chassis, the first and second mechanical fasteners do not overlap.

In an ninth embodiment, the present disclosure provides the absorbent article of any one of the first to eighth embodiments, wherein there is at least one of exposed carrier or exposed adhesive on the carrier between the first mechanical fastener and the first portion of the backing of the second mechanical fastener.

In a tenth embodiment, the present disclosure provides the absorbent article of any one of the first to eighth embodiments, wherein there is no exposed adhesive on the carrier between the first mechanical fastener and the first portion of the backing of the second mechanical fastener.

In an eleventh embodiment, the present disclosure provides the absorbent article of any one of the first to eighth embodiments, wherein the first mechanical fastener and the second mechanical fastener share a common backing.

In a twelfth embodiment, the present disclosure provides the absorbent article of any one of the first to tenth embodiments, wherein the backing of the second mechanical fastener is thinner than a backing of the first mechanical fastener.

In a thirteenth embodiment, the present disclosure provides the absorbent article of any one of the first, third as dependent on the first, fourth, eighth as dependent on the first, third, and fourth embodiments, tenth as dependent on the first, third, and fourth, and eleventh as dependent on the first, third, and fourth embodiments, wherein the first portion of the second surface of the backing is directly bonded to the carrier non-adhesively.

In a fourteenth embodiment, the present disclosure provides the absorbent article of any one of the first to thirteenth embodiments, further comprising a third mechanical fastener on the carrier between the first mechanical fastener and the first portion of the backing of the second mechanical fastener.

In a fifteenth embodiment, the present disclosure provides the absorbent article of any one of the first to fourteenth embodiments, wherein at least one of the first, second, or third mechanical fastener includes openings therethrough.

In a sixteenth embodiment, the present disclosure provides the absorbent article of any one of the first to twelfth embodiments, wherein the first surface of the second mechanical fastener has an area that is free of the second male fastening elements.

In a seventeenth embodiment, the present disclosure provides the absorbent article of the sixteenth embodiment, wherein the first surface of the first portion of the second mechanical fastener is free of the second male fastening elements.

In an eighteenth embodiment, the present disclosure provides the absorbent article of the sixteenth embodiment, wherein the first surface of the second portion of the second mechanical fastener is free of the second male fastening elements.

In a nineteenth embodiment, the present disclosure provides the absorbent article of the sixteenth embodiment, wherein the area that is free of the second male fastening elements is between the first portion and the second portion.

In a twentieth embodiment, the present disclosure provides the absorbent article of any one of the first to nineteenth embodiments, wherein the second male fastening elements are different from the first male fastening elements.

In a twenty-first embodiment, the present disclosure provides the absorbent article of the twentieth embodiment, wherein the second male fastening elements have no loop-engaging heads.

In a twenty-second embodiment, the present disclosure provides the absorbent article of any one of the first to twenty-first embodiments, wherein the absorbent article does not include a loop patch, separate from the backsheet of the chassis.

In a twenty-third embodiment, the present disclosure provides a fastening laminate comprising:
  a carrier;
  a first mechanical fastener comprising first male fastening elements, the first mechanical fastener disposed on the carrier; and
  a second mechanical fastener comprising a backing having a first surface and a second surface opposite the first surface, with second male fastening elements on the first surface of the backing on at least a first portion of the backing or a second portion of the backing, wherein for the first portion of the backing, the second surface of the backing is attached to the carrier at a location that does not include an edge of the carrier, wherein for the second portion of the backing, the backing is not attached to the carrier but is folded over so that at least part of the first surface of the second portion of the backing faces at least part of the first surface of the first portion of the backing.

In a twenty-fourth embodiment, the present disclosure provides the fastening laminate of the twenty-third embodiment, wherein the first portion of the second surface of the backing is adhesively attached to the carrier.

In a twenty-fifth embodiment, the present disclosure provides the fastening laminate of the twenty-third or twenty-fourth embodiment, wherein there is at least one of exposed carrier or exposed adhesive on the carrier between the first mechanical fastener and the first portion of the backing of the second mechanical fastener.

In a twenty-sixth embodiment, the present disclosure provides the fastening laminate of any one of the twenty-third to twenty-fifth embodiments, further comprising adhesive on the second surface of the second portion of the backing.

In a twenty-seventh embodiment, the present disclosure provides the fastening laminate of the twenty-third embodiment, wherein the first portion of the second surface of the backing is directly bonded to the carrier non-adhesively.

In a twenty-eighth embodiment, the present disclosure provides the fastening laminate of the twenty-seventh embodiment, wherein there is no exposed adhesive on the carrier between the first mechanical fastener and the first portion of the backing of the second mechanical fastener.

In a twenty-ninth embodiment, the present disclosure provides the fastening laminate of the twenty-third, twenty-fourth, twenty-seventh, or twenty-eighth embodiments or the twenty-sixth embodiment as dependent on the twenty-third or twenty-fourth embodiment, wherein the first mechanical fastener and the second mechanical fastener share a common backing.

In a thirtieth embodiment, the present disclosure provides the fastening laminate of any one of the twenty-third to twenty-ninth embodiments, wherein the second male fastening elements are disposed on the first surface of both the first portion and the second portion of the backing, and wherein at least some of the second male fastening elements on the first surface of the second portion of the backing abut at least some of the second male fastening elements on the first surface of the first portion of the backing of the second mechanical fastener.

In a thirty-first embodiment, the present disclosure provides the fastening laminate of the thirtieth embodiment, wherein at least some of the second male fastening elements on the first surface of the second portion of the backing engage with at least some of the second male fastening elements on the first surface of the first portion of the backing of the second mechanical fastener.

In a thirty-second embodiment, the present disclosure provides the fastening laminate of any one of the twenty-third to thirty-first embodiments, wherein the first surface of the second mechanical fastener has an area that is free of the second male fastening elements.

In a thirty-third embodiment, the present disclosure provides the fastening laminate of the thirty-second embodiment, wherein the first surface of the first portion of the second mechanical fastener is free of the second male fastening elements.

In a thirty-fourth embodiment, the present disclosure provides the fastening laminate of the thirty-second embodiment, wherein the first surface of the second portion of the second mechanical fastener is free of the second male fastening elements.

In a thirty-fifth embodiment, the present disclosure provides the fastening laminate of the thirty-second embodiment, wherein the area that is free of the second male fastening elements is between the first portion and the second portion.

In a thirty-sixth embodiment, the present disclosure provides a fastening laminate comprising:
  a carrier;
  a first mechanical fastener comprising first male fastening elements, the first mechanical fastener on the carrier; and
  a second mechanical fastener comprising a backing having a first surface and a second surface opposite the first surface, with second male fastening elements on the first surface of the backing, wherein the second mechanical fastener is positioned with the second male fastening elements facing the carrier, wherein an attachment film is adhesively attached to a first portion of the second surface of the backing and to the carrier, but wherein the second surface of the backing is not otherwise attached to the carrier.

In a thirty-seventh embodiment, the present disclosure provides the fastening laminate of the thirty-sixth embodiment, wherein the attachment film is attached to the carrier at a location that does not include an edge of the carrier.

In a thirty-eighth embodiment, the present disclosure provides the fastening laminate of the thirty-sixth or thirty-seventh embodiment, wherein there is exposed adhesive on the carrier between the first mechanical fastener and the second mechanical fastener.

In a thirty-ninth embodiment, the present disclosure provides the fastening laminate of the thirty-sixth or thirty-seventh embodiment, wherein there is no exposed adhesive on the carrier between the first mechanical fastener and the second mechanical fastener.

In a fortieth embodiment, the present disclosure provides the fastening laminate of any one of the thirty-sixth to thirty-ninth embodiments, further comprising adhesive on the second surface of the second portion of the backing.

In a forty-first embodiment, the present disclosure provides the fastening laminate of any one of the thirty-sixth to fortieth embodiments, wherein the second mechanical fastener has an area that is free of the second male fastening elements.

In a forty-second embodiment, the present disclosure provides the fastening laminate of any one of the twenty-third to forty-first embodiments, further comprising a third mechanical fastener on the carrier between the first mechanical fastener and the first portion of the backing of the second mechanical fastener.

In a forty-third embodiment, the present disclosure provides the fastening laminate of any one of the twenty-third to forty-second embodiments, wherein at least one of the first, second, or third mechanical fastener includes openings therethrough.

In a forty-fourth embodiment, the present disclosure provides the fastening laminate of the forty-third embodiment, wherein the openings are diamond- or hexagonal-shaped openings.

In a forty-fifth embodiment, the present disclosure provides the fastening laminate of any one of the twenty-third to forty-fourth embodiments, wherein the second male fastening elements are different from the first male fastening elements.

In a forty-sixth embodiment, the present disclosure provides the fastening laminate of the forty-fifth embodiment, wherein the second male fastening elements have no loop-engaging heads.

In a forty-seventh embodiment, the present disclosure provides the fastening laminate of any one of the twenty-third to twenty-eighth and thirtieth to forty-sixth embodiments except as depending on the twenty-ninth embodiment, wherein the backing of the second mechanical fastener is thinner than a backing of the first mechanical fastener.

In a forty-eighth embodiment, the present disclosure provides the absorbent article or fastening laminate of any one of the first to forty-seventh embodiments, wherein the carrier comprises a nonwoven.

In a forty-ninth embodiment, the present disclosure provides a method of making an absorbent article, the method comprising:
providing a chassis having a topsheet side, a backsheet side, and first and second opposing longitudinal edges extending from a rear waist region to an opposing front waist region;
providing a fastening tab comprising a carrier and a first mechanical fastener disposed on the carrier, the first mechanical fastener having first male fastening elements;
providing a second mechanical fastener, wherein the second mechanical fastener comprises a backing having a first surface and a second surface opposite the first surface, with second male fastening elements on the first surface of the backing;
attaching the carrier to the first longitudinal edge of the chassis on the backsheet side;
attaching the second mechanical fastener to the carrier and to the first longitudinal edge of the chassis on the topsheet side, wherein a first portion of the second surface of the backing of the second mechanical fastener is connected to the carrier and wherein a second portion of the second surface of the backing is attached to the first longitudinal edge of the chassis on the topsheet side. It should be understood that there is a region between the first mechanical fastener and second mechanical fastener that does not include male fastening elements.

In a fiftieth embodiment, the present disclosure provides the method of the forty-ninth embodiment, wherein attaching the second mechanical fastener to the carrier is carried out simultaneously with attaching the second mechanical fastener to the first longitudinal edge of the chassis on the topsheet side.

In a fifty-first embodiment, the present disclosure provides the method of the forty-ninth embodiment, wherein attaching the second mechanical fastener to the carrier precedes attaching the second mechanical fastener to the first longitudinal edge of the chassis on the topsheet side.

In a fifty-second embodiment, the present disclosure provides the method of the fifty-first embodiment, wherein the second portion of the backing is folded over so that at least part of the first surface of the second portion of the backing faces at least part of the first surface of the first portion of the backing, which is attached to the carrier.

In a fifty-third embodiment, the present disclosure provides the method of any one of the forty-ninth to fifty-second embodiments, wherein the first portion of the second surface of the backing is adhesively attached to the carrier.

In a fifty-forth embodiment, the present disclosure provides the method of any one of the forty-ninth to fifty-third embodiments, wherein when the fastening tab is folded at the first longitudinal edge such that the first male fastening elements of the first mechanical fastener contact the topsheet side of the chassis, at least some of the second male fastening elements on the first portion of the first surface of the backing abut at least some of the second male fastening elements on the second portion of the first surface of the backing.

In a fifty-fifth embodiment, the present disclosure provides the method of the fifty-fourth embodiment, wherein at least some of the second male fastening elements on the first portion of the first surface of the backing mechanically engage with at least some of the second male fastening elements on the second portion of the first surface of the backing.

In a fifty-sixth embodiment, the present disclosure provides the method of any one of the forty-ninth and fifty-first to fifty-fifth embodiments except as dependent on the fiftieth embodiment, wherein the second surface of the first portion of the backing is connected to the carrier using an attachment film.

In a fifty-seventh embodiment, the present disclosure provides the method of the fifty-sixth embodiment, wherein the attachment film is adhesively attached to a first portion of the second surface of the backing and to the carrier.

In a fifty-eighth embodiment, the present disclosure provides the method of the fifty-sixth or fifty-seventh embodiment, wherein the attachment film wraps around the first longitudinal edge of the chassis.

In a fifty-ninth embodiment, the present disclosure provides the method of any one of the forty-ninth to fifty-eighth embodiments, wherein when the fastening tab is folded at the first longitudinal edge such that the first male fastening elements of the first mechanical fastener contact the topsheet side of the chassis, the first and second mechanical fasteners do not overlap.

In a sixtieth embodiment, the present disclosure provides the method of any one of the forty-ninth to fifty-ninth embodiments, wherein there is at least one of exposed carrier or exposed adhesive on the carrier between the first mechanical fastener and the first portion of the backing.

In a sixty-first embodiment, the present disclosure provides the method of any one of the forty-ninth to fifty-ninth embodiments, wherein there is no exposed adhesive on the carrier between the first mechanical fastener and the first portion of the backing of the second mechanical fastener.

In a sixty-second embodiment, the present disclosure provides the method of any one of the forty-ninth and fifty-first to sixty-first embodiments except as dependent on the fiftieth embodiment, wherein the fastening tab is provided from a laminated roll of a carrier web with a first mechanical fastening strip and a first portion of a second mechanical fastening strip disposed on the carrier web.

In a sixty-third embodiment, the present disclosure provides the method of the sixty-second embodiment, wherein the roll includes lines of weakness through the carrier web and the fastening strip, wherein the lines of weakness connect a plurality of the laminates together.

In a sixty-fourth embodiment, the present disclosure provides the method of the sixty-second or sixty-third embodiment, wherein the first mechanical fastening strip is provided in a central portion of the carrier web and two of the second mechanical fastening strips are provided between the first mechanical fastening strip and the edges of the carrier web.

In a sixty-fifth embodiment, the present disclosure provides the method of the sixty-fourth embodiment, further comprising slitting the roll through the central portion and in the cross-direction to provide a plurality of the laminates.

In a sixty-sixth embodiment, the present disclosure provides the method of the sixty-fourth embodiment, wherein the roll includes lines of weakness through the carrier web and the fastening strip in the central portion and in the cross-direction, wherein the lines of weakness connect a plurality of the laminates together.

In a sixty-seventh embodiment, the present disclosure provides the method of any one of the sixty-second to sixty-sixth embodiment, wherein the roll is a planetary wound roll.

In a sixty-eighth embodiment, the present disclosure provides the method of any one of the sixty-second to sixty-sixth embodiment, wherein the roll is a level wound roll.

In a sixty-ninth embodiment, the present disclosure provides the method of any one of the sixty-second to sixty-eighth embodiment, wherein the first mechanical fastening strip comprises at least one slit therethrough, where in the slit is interrupted by unslit bridging regions in the first mechanical fastening strip to leave the first mechanical fastening strip intact.

In a seventieth embodiment, the present disclosure provides the method of the sixty-ninth embodiment, the slit forms multiple strands attached to each other at intact bridging regions, the method further comprising and separating at least some of the multiple strands between at least some of the bridging regions.

Various modifications and alterations of this disclosure may be made by those skilled the art without departing from the scope and spirit of the disclosure, and it should be understood that this invention is not to be unduly limited to the illustrative embodiments set forth herein. All patents and patent applications cited above are hereby incorporated by reference into this document in their entirety.

What is claimed is:

1. An absorbent article comprising:
   a chassis with a topsheet side, a backsheet side, and first and second opposing longitudinal edges extending from a rear waist region to an opposing front waist region; and
   a fastening tab comprising a carrier, a first mechanical fastener having first male fastening elements, the first mechanical fastener disposed on the carrier, and a second mechanical fastener,
   wherein the second mechanical fastener comprises a backing having a first surface and a second surface opposite the first surface, wherein for a first portion of the backing, the second surface of the backing is connected to the carrier, wherein for a second portion of the backing, the second surface of the backing is attached to the first longitudinal edge of the chassis on the topsheet side, wherein the carrier is attached to the first longitudinal edge of the chassis on the backsheet side, and wherein for at least one of the first portion or the second portion of the backing, second male fastening elements are disposed on the first surface of the backing, and wherein when the fastening tab is folded at the first longitudinal edge, the first male fastening elements of the first mechanical fastener contact the topsheet side of the chassis.

2. The absorbent article of claim 1, wherein the first portion of the second surface of the backing is adhesively attached to the carrier.

3. The absorbent article of claim 1, wherein the second male fastening elements are disposed on the first surface of both the first portion and the second portion of the backing, wherein when the fastening tab is folded at the first longitudinal edge such that the first male fastening elements of the first mechanical fastener contact the topsheet side of the chassis, at least some of the second male fastening elements on the first surface of the first portion of the backing abut at least some of the second male fastening elements on the first surface of the second portion of the backing.

4. The absorbent article of claim 1, wherein the first surface of the second mechanical fastener has an area that is free of the second male fastening elements.

5. The absorbent article of claim 4, wherein the first surface of the first portion of the second mechanical fastener is free of the second male fastening elements.

6. The absorbent article of claim 1, wherein the second surface of the first portion of the backing is connected to the carrier using an attachment film.

7. The absorbent article of claim 1, wherein when the fastening tab is folded at the first longitudinal edge such that the first male fastening elements of the first mechanical fastener contact the topsheet side of the chassis, the first and second mechanical fasteners do not overlap.

8. The absorbent article of claim 1, wherein there is exposed adhesive on the carrier between the first mechanical fastener and the first portion of the backing of the second mechanical fastener.

9. A fastening laminate comprising:
a carrier;
a first mechanical fastener comprising first male fastening elements, the first mechanical fastener disposed on the carrier; and
a second mechanical fastener comprising a backing having a first surface and a second surface opposite the first surface, with second male fastening elements on the first surface of the backing on at least a first portion of the backing or a second portion of the backing, wherein for the first portion of the backing, the second surface of the backing is attached to the carrier at a location that does not include an edge of the carrier, wherein for the second portion of the backing, the backing is not attached to the carrier but is folded over so that at least part of the first surface of the second portion of the backing faces at least part of the first surface of the first portion of the backing.

10. The fastening laminate of claim 9, wherein the second male fastening elements are disposed on the first surface of both the first portion and the second portion of the backing, and wherein at least some of the second male fastening elements on the first surface of the second portion of the backing engage with at least some of the second male fastening elements on the first surface of the first portion of the backing of the second mechanical fastener.

11. The fastening of claim 9, wherein the first surface of the second mechanical fastener has an area that is free of the second male fastening elements.

12. The fastening laminate of claim 11, wherein the first surface of the first portion of the second mechanical fastener is free of the second male fastening elements.

13. The fastening laminate of claim 9, wherein the second surface of the first portion of the backing is adhesively attached to the carrier, and wherein there is exposed adhesive on the carrier between the first mechanical fastener and the first portion of the backing of the second mechanical fastener.

14. A fastening laminate comprising:
a carrier;
a first mechanical fastener comprising first male fastening elements, the first mechanical fastener disposed on the carrier; and
a second mechanical fastener comprising a backing having a first surface and a second surface opposite the first surface, with second male fastening elements on the first surface of the backing, wherein the second mechanical fastener is positioned with the second male fastening elements facing the carrier, wherein an attachment film is adhesively attached to a first portion of the second surface of the backing and to the carrier, but wherein the second surface of the backing is not otherwise attached to the carrier.

15. The fastening laminate of claim 14, wherein at least one of the following conditions is met:
at least one of the first mechanical fastener or the second mechanical fastener includes openings therethrough;
there is a third mechanical fastener disposed on the carrier between the first mechanical fastener and the first portion of the backing of the second mechanical fastener; or
the second male fastening elements are different from the first male fastening elements.

16. The fastening laminate of claim 14, wherein there is exposed adhesive on the carrier between the first mechanical fastener and the second mechanical fastener.

17. The fastening laminate of claim 14, further comprising adhesive on the second surface of a second portion of the backing.

18. The fastening laminate of claim 14, wherein the attachment film is attached to the carrier at a location that does not include an edge of the carrier.

19. The fastening laminate of claim 9, wherein at least one of the following conditions is met:
at least one of the first mechanical fastener or the second mechanical fastener includes openings therethrough;
there is a third mechanical fastener disposed on the carrier between the first mechanical fastener and the first portion of the backing of the second mechanical fastener; or
the second male fastening elements are different from the first male fastening elements.

20. The absorbent article of claim 1, wherein at least one of the following conditions is met:
at least one of the first mechanical fastener or the second mechanical fastener includes openings therethrough;
there is a third mechanical fastener disposed on the carrier between the first mechanical fastener and the first portion of the backing of the second mechanical fastener; or
the second male fastening elements are different from the first male fastening elements.

* * * * *

UNITED STATES PATENT AND TRADEMARK OFFICE
CERTIFICATE OF CORRECTION

PATENT NO. : 10,973,710 B2  
APPLICATION NO. : 15/527570  
DATED : April 13, 2021  
INVENTOR(S) : Mark Peltier et al.

Page 1 of 1

It is certified that error appears in the above-identified patent and that said Letters Patent is hereby corrected as shown below:

In the Claims

<u>Column 33</u>
Line 34, in Claim 11, after "fastening" insert -- laminate --.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*